(12) United States Patent
Sharma et al.

(10) Patent No.: US 7,417,027 B2
(45) Date of Patent: Aug. 26, 2008

(54) LINEAR AND CYCLIC MELANOCORTIN RECEPTOR-SPECIFIC PEPTIDES

(75) Inventors: Shubh D. Sharma, Cranbury, NJ (US); Annette M. Shadiack, Somerset, NJ (US); Wei Yang, Edison, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 570 days.

(21) Appl. No.: 10/756,212

(22) Filed: Jan. 12, 2004

(65) Prior Publication Data

US 2005/0038230 A1 Feb. 17, 2005

Related U.S. Application Data

(63) Continuation of application No. PCT/US02/22196, filed on Jul. 11, 2002.

(60) Provisional application No. 60/304,836, filed on Jul. 11, 2001.

(51) Int. Cl.
*A61K 38/08* (2006.01)
*A61K 38/07* (2006.01)

(52) U.S. Cl. ............... 514/17; 514/18; 530/329; 530/330; 530/331

(58) Field of Classification Search ............... None
See application file for complete search history.

(56) References Cited

U.S. PATENT DOCUMENTS

| | | | |
|---|---|---|---|
| 3,853,836 A | 12/1974 | Greven | |
| 3,862,928 A | 1/1975 | De Wied et al. | |
| 5,420,109 A | 5/1995 | Suto et al. | |
| 5,576,290 A * | 11/1996 | Hadley | 514/11 |
| 5,731,408 A | 3/1998 | Hadley et al. | |
| 6,054,556 A | 4/2000 | Hruby et al. | |
| 7,049,398 B1 * | 5/2006 | Sharma et al. | 530/328 |

FOREIGN PATENT DOCUMENTS

| | | |
|---|---|---|
| FR | 2 691 465 | 11/1993 |
| WO | WO 96/38471 | 12/1996 |
| WO | WO 98/10068 | 3/1998 |
| WO | WO 98/27113 | 6/1998 |
| WO | PCT/US98/03298 | 5/1999 |
| WO | WO 99/54358 | 10/1999 |
| WO | WO 00/05263 | 2/2000 |
| WO | WO 00/58361 | 10/2000 |
| WO | WO 01/13112 | 2/2001 |
| WO | WO 01/30808 | 5/2001 |
| WO | WO 01/85930 | 11/2001 |
| WO | WO 01/90140 | 11/2001 |
| WO | WO 02/085925 | 10/2002 |
| WO | PCT/US02/21443 | 1/2003 |

OTHER PUBLICATIONS

Youngquist et al. "Generation and screening of combinatorial peptide libraries designed for rapid sequencing by mass spectrometry" J. of Am. Chem. Soc. vol. 117, No. 14: Apr. 12, 1995. pp. 3900-3906.*

* cited by examiner

*Primary Examiner*—Anish Gupta
(74) *Attorney, Agent, or Firm*—Stephen A. Slusher

(57) ABSTRACT

Linear and cyclic peptides are provided specific to one or melanocortin receptors, and which exhibit agonist, antagonist, or mixed agonist-antagonist activity. In one embodiment, a linear peptide of the following general formula is provided:

$$\left[R_1-\underset{\underset{R_7}{|}}{N}-\right]_m\left[\underset{\underset{O}{||}}{C}-\underset{\underset{T_2}{|}}{C}-\right]_n\left[\underset{\underset{R_3}{|}}{N}\underset{T_3}{-}\underset{\underset{O}{||}}{C}-\underset{\underset{R_7}{|}}{C}-\right]\left[\underset{\underset{R_7}{|}}{N}\underset{T_4}{-}\underset{\underset{O}{||}}{C}-\underset{\underset{R_5}{|}}{C}-\right]\left[\underset{\underset{R_7}{|}}{N}\underset{T_5}{-}\underset{\underset{O}{||}}{C}-\right]_p\left[\underset{\underset{T_9}{|}}{N}-\underset{\underset{O}{||}}{C}-R_6\right]_q$$

8 Claims, 3 Drawing Sheets

LINEAR AND CYCLIC MELANOCORTIN RECEPTOR-SPECIFIC PEPTIDES

CROSS-REFERENCE TO RELATED APPLICATIONS

This application is a continuation application of International Patent Application Ser. No. PCT/US02/22196, Publication No. WO 03/006620, entitled "Linear and Cyclic Melanocortin Receptor-Specific Peptides", filed on Jul. 11, 2002, and the specification thereof is incorporated herein by reference.

This application claims the benefit of the filing of U.S. Provisional Patent Application Serial No. 60/304,836, entitled "Linear and Cyclic Melanocortin Receptor-Specific Peptides", filed on Jul. 11, 2001, and the specification thereof is incorporated herein by reference.

BACKGROUND OF THE INVENTION

1. Field of the Invention (Technical Field)

The present invention provides both linear and cyclic peptides that are specific for one or more melanocortin receptors, and which may be used in the treatment of a wide variety of diseases.

2. Background Art

Melanocortin Receptors. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues.

Peptides specific for melanocortin receptors have been reported to have a wide variety of biological activities, including effects upon pigmentation and steroidogenesis, known to be mediated by MSH (melanocyte stimulating hormone) and ACTH receptors. Several studies have documented the presence of melanotropin receptors on primary human melanoma cells (Tatro J B, Atkins M, Mier J W, et al. Melanotropin receptors demonstrated in situ in human melanoma. *J Clin Invest*, 85:1825-1832, 1990). Melanotropin receptors have been reported as markers for melanotic and amelanotic human melanoma tumors (Sharma S D, Granberry M E, Jiang J, et al. Multivalent melanotropic peptide and fluorescent macromolecular conjugates: new reagents for characterization of melanotropin receptors. *Bioconjug Chem* 5:591-601, 1994; Sharma S D, Jiang J, Hadley M E, et al. Melanotropic peptide-conjugated beads for microscopic visualization and characterization of melanoma melanotropin receptors. *Proc Natl Acad Sci USA* 93(24):13715-13720, 1996). In particular, the presence of MC1-R has been demonstrated in human melanoma cells by an antibody to MC1-R (Xia Y, Skoog V, Muceniece R, et al. Polyclonal antibodies against human melanocortin MC-1 receptor: Preliminary immunohistochemical localization of melanocortin MC1 receptor to malignant melanoma cells. *European J Pharmacol* 288:277-283, 1995). MC1-R is a G protein-coupled, 7-transmembrane receptor expressed in skin-cell melanocytes and shares some degree of homology with related receptors MC2-R, MC3-R, MC4-R and MC5-R. Each of these receptors can bind various peptide analogs that contain a common melanotropic pharmacophore, His-Phe-Arg-Trp (SEQ ID NO: 1), which describes the 6-9 sequence of the alpha-melanocyte stimulating hormone (α-MSH).

Prior to molecular characterization of the MC receptors, α-MSH analogs were labeled with the radioisotope Indium-111 and used in melanoma imaging studies (Wraight E P, Bard D R, Maughan T S, et al. The use of a chelating derivative of alpha melanocyte stimulating hormone for the clinical imaging of malignant melanoma. *Brit J Radiology* 65: 112-118, 1992; Bard D R, Knight C G and Page-Thomas D P. A chelating derivative of alpha-melanocyte stimulating hormone as a potential imaging agent for malignant melanoma. *Brit J Cancer* 62:919-922, 1990; Bard D R, Knight C G, Page-Thomas D P. Targeting of a chelating derivative of a short chain analogue of alpha-melanocyte stimulating hormone to Cloudman S91 melanomas. *Biochem Soc Trans* 18:882-883, 1990). Linear and cyclic disulfide-containing peptides have been identified and used for melanoma imaging and appear to be non-selective among MC receptors (Chen J and Quinn T P. Alpha melanocyte stimulating hormone analogues Tc-99 m/Re-188 labeling and their pharmacokinetics in malignant melanoma bearing mice. *J Nucl Med* 39: 222p, 1998; Giblin M F, Wang N, Hoffman T J, et al. Design and characterization of alpha-melanotropin peptide analogs cyclized through rhenium and technetium metal coordination. *Proc Natl Acad Sci USA* 95(22):12814-12818, 1998). In later studies, the cyclic peptide reported by Giblin and coworkers was also found to localize in the brain (Wang N N, Giblin M F, Hoffman T J, et al. In vivo characterization of Tc-99m and Re-188 labeled cyclic melanotropin peptide analogues in a murine melanoma model. *J Nucl Med* 39: 77p, 1998 and corresponding poster presentation at the 45th Society of Nuclear Medicine Meeting, Toronto, June 1998). It has been recently reported that the response of human melanocytes to UV radiation is mediated by α-MSH induced activation of the cAMP pathway through the MC1-R (Im S, Moro O, Peng F, et al. Activation of the cyclic AMP pathway by alpha-melanotropin mediates the response of human melanocytes to ultraviolet B radiation. *Cancer Res* 58: 47-54, 1998).

MC4-R is also a G protein-coupled, 7-transmembrane receptor, but is believed to be expressed primarily in the brain. Inactivation of this receptor by gene targeting has been reported to result in mice with the maturity-onset obesity syndrome that is associated with hyperphagia, hyperinsulinemia, and hyperglycemia (Huszar D, Lynch C A, Fairchild-Huntress V, et al. Targeted disruption of the melanocortin-4 receptor results in obesity in mice. *Cell* 88:131-141, 1997). MC4-R is a molecular target for therapeutic intervention in energy homeostasis.

Alpha-MSH has been described as a potent anti-inflammatory agent in all major forms of inflammation (Star R A, Rajora N, Huang J, Stock R C, Catania A, and Lipton J M. Evidence of autocrine modulation of macrophage nitric oxide synthase by alpha-melanocyte stimulating hormone. *Proc Natl Acad Sci USA* 92:8016-8020, 1995; Getting S J, and Perretti M. MC3-R as a novel target for antiinflammatory therapy. *Drug News and Perspectives* 13:19-27, 2000). Implication of both MC1-R and MC3-R receptors in anti-inflammatory processes has been stressed. In particular, the activation of these MC receptors by melanocortin receptor agonists has been reported to inhibit the expression of nitric oxide synthase and subsequent nitric oxide production.

Significant work has been done in determining the structure of melanocortin receptors, including both the nucleic acid sequences encoding for the receptors and the amino acid sequences constituting the receptors. See, for example, International Patent Application Nos. PCT/US98/12098 and PCT/

US99/16862 and U.S. Pat. No. 5,994,087. A large number of ligands specific for melanocortin receptors, both agonists and antagonists, have also been developed. See, for example, International Patent Application Nos. PCT/US00/16396, commonly owned with this application and with common inventors (metallopeptides specific for MC receptors); PCT/US98/03298 (iodo group-containing melanocortin receptor-specific linear peptide); PCT/GB99/01388 (MC1-R specific linear peptides); PCT/GB99/01195 (MC3-R, MC4-R and MC5-R specific cyclic peptides); PCT/US99/04111 (MC1-R specific peptide antagonists for melanoma therapy); PCT/US99/09216 (isoquinoline compounds as melanocortin receptor ligands); PCT/US99/13252 (spiropiperdine derivatives as melanocortin receptor agonists); and U.S. Pat. No. 6,054,556 (cyclic lactam peptides as MC1-R, MC3-R, MC4-R and MC5-R antagonists). In addition, a large number of patents teach various methods of screening and determining melanocortin receptor-specific compounds, as for example International Patent Application Nos. PCT/US97/15565, PCT/US98/12098 and PCT/US99/16862 and U.S. Pat. Nos. 5,932,779 and 5,994,087.

In general, compounds specific for MC1-R are believed to be useful for treatment of melanoma, including use as radiotherapeutic or drug delivery agent, and as diagnostic imaging agents, particularly when labeled with a diagnostic radionuclide. Compounds specific for MC3-R, MC4-R or MC5-R are believed to be useful in regulation of energy homeostasis, including use as agents for attenuating food intake and body weight gain, for use in treatment of anorexia, as a weight gain aid, for treatment of obesity, and other treatment of other food intake and metabolism-related purposes. Compounds specific for MC3-R and MC4-R, among other melanocortin receptors, can be used as agents for treatment of sexual dysfunction, including male erectile dysfunction. Compounds specific for MC3-R and MC4-R, among other melanocortin receptors, can be used to regulate blood pressure, heart rate and other neurophysiologic parameters. Other melanocortin receptor peptides can be used as tanning agents, to increase melanin production, such as peptides that are MC1-R agonists. Compounds specific for MC1-R and MC3-R may be useful in regulation of inflammatory processes.

There remains a significant need for ligands with high specificity for discrete melanocortin receptors, as well as ligands or compounds that are either agonists or antagonists of specific melanocortin receptors. High affinity peptide ligands of melanocortin receptors can be used to exploit varied physiological responses associated with the melanocortin receptors, either as agonists or antagonists. In addition, melanocortin receptors have an effect on the activity of various cytokines, and high affinity peptide ligands of melanocortin receptors can be used to regulate cytokine activity.

SUMMARY OF THE INVENTION (DISCLOSURE OF THE INVENTION)

In one embodiment the invention provides a peptide comprising the sequence $S_1$-$S_2$-$S_3$-$S_4$-$S_5$, wherein:

$S_1$ is any functionality that potentiates the intrinsic activity of the remainder of the peptide, including but not limited to providing an auxiliary or secondary receptor contact; including any of a variety of amino acids and non-peptide groups, including an amino acid chain from one to about four neutral or charged L- or D-configuration amino acid residues, and further wherein if $S_1$ is a non-peptide group, it comprises a linear or branched alkyl, aryl, alkene, alkenyl or aralkyl chain;

$S_2$ is absent, or if provided, a residue acting as a spacer, and preferably one or more natural or unnatural aliphatic amino acids, including Gly, Ala, Val, Leu or Nle, of either L- or D-configuration;

$S_3$ is L- or D-Phe, Phe(4-Cl), Phe(2,4-diCl), Phe(3,4-diCl), Phe(4-NO$_2$), Phe(4-Me), Phe(4-Phenyl), Hphe, Pgl, Trp, Nal 1, Nal 2, Bip, Dip, Bpa, Ser(Bzl), Lys(Z), Lys(Z-2'Br), Lys(Bz), Thr(Bzl), Cys(Bzl), Tyr(BzlCl$_2$) or any natural or unnatural L- or D-amino acid with an aromatic side chain group, wherein the aromatic ring is optionally functionalized with halogen, alkyl or aryl groups;

$S_4$ is L- or D-Lys, Arg, Orn, Dpr, Dbu, p-amino-Phe or any natural or unnatural L- or D-amino acid with a positively charged side chain, and preferably an L-configuration cationic amino acid;

$S_5$ is an L- or D-amino acid with an aromatic side chain, and optionally comprising one or more additional amino acids, and further optionally comprising a terminus group, including Phe, Phe(4-Cl), Phe(2,4-diCl), Phe(3,4-diCl), Phe(4-NO$_2$), Phe(4-Me), Phe(4-Phenyl), Hphe, Pgl, Trp, Nal 1, Nal 2, Bip, Dip, Bpa, Ser(Bzl), Lys(Z), Lys(Z-2'Br), Lys(Bz), Thr(Bzl), Cys(Bzl), Tyr(BzlCl$_2$), N-alkylated or arylated derivatives of any of the foregoing, or a des-carboxylamino acid corresponding to any of the foregoing, in which event $S_5$ comprises a substituted amide function of the $S_4$ residue.

In yet another embodiment, the invention provides a peptide, comprising the sequence $S_1$-$S_2$-D-Phe(4-Cl)-$S_4$-$S_5$, wherein:

$S_1$ is heptanoyl, 2'-naphthylacetyl, 7'-amino-heptanoyl, 2'-chlorophenylacetyl, 3'-chlorophenylacetyl, 4'-chlorophenylacetyl, 4'-phenylbutylaminocarbonyl, 3'-phenylbutylaminocarbonyl, 4'-bromophenyl-acetyl, 3-4-dichlorophenyl-acetyl, 2,4-dichlorophenyl-acetyl, 4-biphenyl-acetyl, 2-naphthoyl, Ph-(CH$_2$)$_2$NH, 3'-phenylpropanecarbonyl, 2'-naphthoyl-Pip, 2'-naphthylacetyl, 2'-bromophenyl-acetyl, 4'-CF$_3$phenyl-acetyl, 3'-CF$_3$phenyl-acetyl, 2'-CF$_3$phenyl-acetyl, 3',5'-CF$_3$phenylacetyl, 2',5'-CF$_3$phenylacetyl, 4'-Mephenyl-acetyl, 3'-Mephenyl-acetyl, 2'-Mephenyl-acetyl, 7'-amino-heptonoyl, beta-Ala, 4-aminoBytyl, 5-aminoValeryl, 6-aminoCaproyl, aminoTranexamyl, Cmpi or 3',4'-Cl$_2$phenylacetyl;

$S_2$ is absent or is Ser(Bzl), Ala, D-Ala, beta-Ala, Val, Leu, Chg, Aib, Tle, 1-amino-1cyclohexanecarbonyl, Inp, CO(CH$_2$)$_2$NH, CO(CH$_2$)$_2$CO, Pip, MeThr(Bzl), Thr(Bzl) or D-Thr(Bzl);

$S_4$ is Arg, D-Arg, (Nlys)Gly, Trp, Lys, homoLys, Dpr(beta-Ala), alpha-(N-amidino-4'-piperidine)Gly, (4'-guanidino)Gly, (4'-guanidino)Phe, D-(4'-guanidino)Phe, beta-(N-amidino-4'-peperidine)Ala or homo-Ala-4'-pip(N-amidino); and $S_5$ is Trp, Trp-OH, Trp-NH$_2$, Trp-Cys-NH$_2$, D-Trp, D-Trp-NH$_2$, Trp-Val-NH$_2$, 3'-Pya-NH$_2$, Phe-NH$_2$, MeTrp-NH$_2$, beta-Ala-Trp-NH$_2$, aminobutylamide, Nal 1-NH$_2$, D-Nal 1-NH$_2$, Nal 2-NH$_2$, D-Nal 2-NH$_2$, Tic-NH$_2$, D-Tic-NH$_2$, 1'-aminoindan, 1'-aminoindane-1-carboxyl-NH$_2$, Aic-NH$_2$, Atc-NH$_2$, Disc-NH$_2$, Tpi-NH$_2$, D-Tpi-NH$_2$, Tiq-NH$_2$, D-Tiq-NH$_2$, tryptamide, NMe-tryptamide, alpha-Me-tryptamide, 2'-(4'-methylphenyl)ethylamide, 3',4'-Cl$_2$)phenylmethylamide, 3'-phenylpropylamide, 2',4'-dichlorobenzylamide, 3'-(1H-imidazol)propylamide, 4-phenyl-piperidine-4-carbonamide, 3-phenyl-1-propylamide, 2,4-dichlorophenethylamide, S-(−)-1-(2-naphthyl)ethylamide, S-(−)-1-(1-naphthyl)ethylamide, 2'-methyl benzylamide, 4'-methylbenzylamide, 2',2'-diphenylethylamide, 1-(2-pyridyl)piperazine, N-benzylmethylamide, histamide, R-(+)-1-(2-Naphthyl)ethylamide, Trp-Asp-NH$_2$, Trp-Asp-Phe-NH$_2$, Asp-Trp-NH$_2$, Ala-Trp-NH$_2$, Trp-Ala-NH$_2$, phenethylamide or Trp-Asp-OH.

Representative peptides of the formula S$_1$-S$_2$-D-Phe(4-Cl)-S$_4$-S$_5$ include 7'-amino-heptanoyl-Ser(Bzl)-D-Phe(4-Cl)-Arg-Trp, 7'-amino-heptanoyl-Ser(Bzl)-D-Phe(4-Cl)-Arg-Trp-NH$_2$, 7'-amino-heptanoyl-Ser(Bzl)-D-Phe(4-Cl)-Arg-Trp-Ala-NH$_2$, 7'-amino-heptanoyl-Ser(Bzl)-D-Phe(4-Cl)-Arg-Trp-Asp-Phe-NH$_2$, 7'-amino-heptanoyl-Ser(Bzl)-D-Phe(4-Cl)-Arg-Trp-Asp-N H$_2$, heptanoyl-Thr(Bzl)-D-Phe(4-Cl)-Arg-Trp-NH$_2$, 7'-amino-heptanoyl-Ser(Bzl)-D-Phe(4-Cl)-Arg-MeTrp-NH$_2$, heptanoyl-Ser(Bzl)-D-Phe(4-Cl)-Arg-MeTrp-NH$_2$, 7'-amino-heptanoyl-Ser(Bzl)-D-Phe(4-Cl)-Arg-Tryptamide, 7'-amino-heptanoyl-Ser(Bzl)-D-Phe(4-Cl)-Arg-NMe-Tryptamide, 7'-amino-heptanoyl-Ser(Bzl)-D-Phe(4-Cl)-Arg-alpha-Me-Tryptamide, 7'-amino-heptanoyl-Ser(Bzl)-D-Phe(4-Cl)-Arg-S-(−)-1-(1-Naphthyl)ethylamide, 7'-amino-heptanoyl-Ser(Bzl)-D-Phe(4-Cl)-Arg-Nal 1-NH$_2$, 7'-amino-heptanoyl-Ser(Bzl)-D-Phe(4-Cl)-Arg-D-Nal 2-NH$_2$, 7'-amino-heptanoyl-Ser(Bzl)-D-Phe(4-Cl)-Arg-Nal 2-NH$_2$, 2'-naphthylacetyl-Ala-D-Phe(4-Cl)-Arg-Trp-NH$_2$, 4'phenylbutyryl-Ala-D-Phe(4-Cl)-Arg-Trp-NH$_2$, 3',4'-dichlorophenyl-acetyl-Ala-D-Phe(4-Cl)-Arg-Trp-NH$_2$, and 3'-CF$_3$phenyl-acetyl-Ala-D-Phe(4-Cl)-Arg-Trp-NH$_2$.

In yet another embodiment, the invention provides a peptide comprising the sequence 7'-amino-heptanoyl-S$_2$-D-Phe(4-Cl)-S$_4$-S$_5$, wherein S$_2$, S$_4$ and S$_5$ are as defined above. Peptides of the formula 7'-amino-heptanoyl-S$_2$-D-Phe(4-Cl)-S$_4$-S$_5$ include each of the representative peptides of the preceding paragraph wherein the initial residue is 7'-amino-heptanoyl.

In yet another embodiment, the invention provides a peptide comprising the sequence S$_1$-S$_2$-S$_3$-S$_4$-S$_5$, wherein S$_1$, S$_2$, S$_4$ and S$_5$ are as defined above, and S$_3$ is Phe, D-Phe, Phe(4-Cl), D-Phe(4-Cl), Phe(3-Cl), D-Phe(3-Cl), Phe(2-Cl), D-Phe(2-Cl), D-Phe(3,4-diCl), MePhe, D-MePhe, D-Tic, D-Tpi, D-Nal 2, Arg, D-Phe(3,4-F$_2$), D-Tiq, D-Me(homo)Phe or D-EtPhe. Representative peptides of the formula S$_1$-S$_2$-S$_3$-S$_4$-S$_5$ include the foregoing described peptides and 7'-amino-heptanoyl-Ser(Bzl)-D-Nal 2-Arg-Trp-NH$_2$, 7'-amino-heptanoyl-Ala-D-Nal 2-Arg-Trp-NH$_2$, Ser(Bzl)-D-Nal 2-Arg-Trp-NH$_2$ and Ser(Bzl)-D-Nal 2-Arg-D-Trp-NH$_2$.

The invention further comprises a method for stimulating sexual response in a mammal, comprising administering a pharmaceutically sufficient amount of a composition comprising a peptide or pharmaceutically acceptable salt thereof. In this method, the mammal may be a male or a female. The composition may further comprise a pharmaceutically acceptable carrier. In the method, administering may include administering by a method of administration such as administration by injection, administration through mucous membranes, buccal administration, oral administration, dermal administration, inhalation administration, nasal administration, parenteral administration, pulmonary administration, ocular administration, sublingual administration and vaginal adminstration. In the event of nasal administration, it may be nasal administration of a metered amount of a formulation comprising an aqueous buffer.

The invention further comprises a method for inhibiting food uptake in a mammal, comprising administering a pharmaceutically sufficient amount of a composition comprising a peptide or pharmaceutically acceptable salt thereof, and particularly an MC3/4-R selective agonist. The composition may further comprise a pharmaceutically acceptable carrier. In the method, administering may include administering by a method of administration such as administration by injection, administration through mucous membranes, buccal administration, oral administration, dermal administration, inhalation administration, nasal administration, parenteral administration, pulmonary administration, ocular administration and sublingual administration. In the event of nasal administration, it may be nasal administration of a metered amount of a formulation comprising an aqueous buffer.

The invention further comprises a method for increasing weight gain in a mammal, comprising administering a pharmaceutically sufficient amount of a composition comprising a peptide or pharmaceutically acceptable salt thereof, and particularly an MC4/5-R selective antagonist. The composition may further comprise a pharmaceutically acceptable carrier. In the method, administering may include administering by a method of administration such as administration by injection, administration through mucous membranes, buccal administration, oral administration, dermal administration, inhalation administration, nasal administration, parenteral administration, pulmonary administration, ocular administration and sublingual administration. In the event of nasal administration, it may be nasal administration of a metered amount of a formulation comprising an aqueous buffer.

A primary object of the present invention is a melanocortin receptor-specific pharmaceutical for use in treatment of sexual dysfunction.

A second object is to provide a melanocortin receptor-specific pharmaceutical for use in treatment of male sexual dysfunction, including erectile dysfunction.

Another object is to provide a melanocortin receptor-specific pharmaceutical for use in treatment of female sexual dysfunction.

Another object is to provide a melanocortin receptor-specific pharmaceutical for use in treatment of eating disorders.

Another object is to provide a melanocortin receptor-specific pharmaceutical for use in treatment of which is effective by nasal administration.

Another object of this invention is to provide compounds which are specific for melanocortin receptors MC3-R and/or MC4-R and/or MC5-R and which are agonists or antagonists.

Other objects, advantages and novel features, and the further scope of applicability of the present invention, will be set forth in part in the detailed description to follow, taken in conjunction with the accompanying drawings, and in part will become apparent to those skilled in the art upon examination of the following, or may be learned by practice of this invention. The objects and advantages of this invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Figure 1:
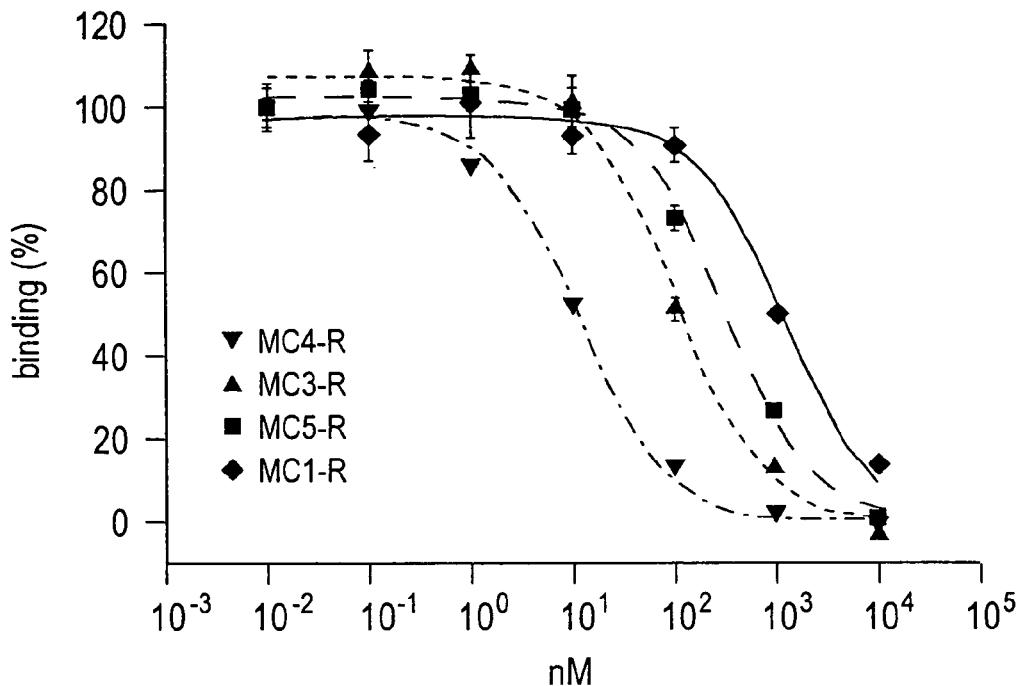
FIG. 1 is a graph of displacement of I$^{125}$-NDP-α-MSH bound to MC1-R, MC3-R, MC4-R and MC5-R using varying concentrations of 7'-amino-heptanoyl-Ser(Bzl)-D-Phe(4-Cl)-Arg-Trp-NH$_2$. The x-axis is percent 1$^{125}$-NDP-α-MSH binding, and the y-axis is concentration.

Best Modes for Carrying Out the Invention

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino adds. For the most part, the peptides of this invention comprise fewer than 100 amino acids, and preferably fewer than 60 amino acids, and most preferably ranging from about 2 to 20 amino acids. The amino acids forming all or a part of a peptide may be naturally occurring amino adds, stereoisomers and modifications of such amino acids, non-protein amino acids, post-translationally modified amino acids, enzymatically modified amino acids, constructs or structures designed to mimic amino adds, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. In addition, the following abbreviations have the meanings giving:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| 7-Ahept | 7-amino heptanoic acid |
| Aib | alpha-aminoisobutyric acid |
| Aic | 2-aminoindane-2-carboxylic acid |
| 6-Ahx | 6-amino hexanoic acid |
| Amb | 4-(aminomethyl)-benzoic acid |
| Amc | 4-(aminomethyl)-cyclohexane carboxylic acid |
| 7'-amino-heptanoyl | NH$_2$—(CH$_2$)$_6$CO— |
| 8-Aoc | 8-amino octanoic acid |
| Arg(Tos) | N$^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Bip | biphenylalanine |
| Bzl | benzyl |
| Bz | benzoyl |
| Cha | cyclohexylalanine |
| Chg | cyclohexylglycine |
| Cmpi | 4-caboxymethyl-piperazine |
| Dip | 3,3-diphenylalanine |
| Disc | 1,3-dihydro-2H-isoindolecarboxylic acid |

-continued

| | |
|---|---|
| Dpr(beta-Ala) | $N^{beta}$-(3-aminopropionyl)-alpha,beta-diaminopropionic acid |
| Et— | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| heptanoyl | $CH_3$—$(CH_2)_5CO$— |
| Hphe | homophenylalanine |
| HyP | hydroxy proline |
| Idc | indoline-2-carboxylic acid |
| Igl | indanylglycine |
| Inp | isonipecotic acid |
| Lys(Z) | N-epsilon-benzyloxycarbonyl-lysine |
| Me— | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl-$CH_2CO$— |
| (Nlys)Gly | N-(4-aminobutyl)-glycine |
| (N—PhEt)Nal 2 | N(2-phenylethyl)-3-(2-naphthyl) alanine |
| OcHx | cyclohexyl ester |
| Phg | phenylglycine |
| pF—Phe | para-fluoro-phenylalanine |
| Phe(4-Br) | 4-bromo-phenylalanine |
| Phe(4-$CF_3$) | 4-trifluoromethyl-phenylalanine |
| Phe(4-Cl) | 4-chloro-phenylalanine |
| Phe(2-Cl) | 2 chloro-phenylalanine |
| Phe(2,4-diCl) | 2,4,-dichloro-phenylalanine |
| Phe(3,4-diCl) | 3,4,-dichloro-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-$NO_2$) | 4-nitro-phenylalanine |
| Pip | pipecolic acid |
| 3-Pya | 3-pyridylalanine |
| Qal(2') | beta-(2-quinolyl)-alanine |
| Sal | 3-styrylalanine |
| Sar | sarcosine |
| Ser(Bzl) | O-benzyl-serine |
| TFA | trifluoroacetyl |
| Tic | 1,2,3,4-tetrahydroisoquinoline-3-carboxylic acid |
| Tiq | 1,2,3,4-tetrahydroisoquinoline-1-carboxytic acid |
| Tle | tert-butylalanine |
| Tpi | 1,2,3,4-tetrahydronorharman-3-carboxylic acid |
| Tyr(Bzl) | O-benzyl-tyrosine |
| Tyr(BzlDiCl 2,6) | O-(2,6 dichloro)benzyl-tyrosine |
| Z | benzyloxycarbonyl |

In the listing of compounds according to the present invention, conventional amino acid residues have their conventional meaning as given in Chapter 2400 of the *Manual of Patent Examining Procedure*, 7th Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

A single amino acid, including stereoisomers and modifications of naturally occurring protein amino acids, non-protein amino adds, post-translationally modified amino acids, enzymatically synthesized amino acids, derivatized amino acids, constructs or structures designed to mimic amino acids, and the like, including all of the foregoing, is sometimes referred to herein as a "residue."

The peptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptides of this invention may be synthesized by solid-phase synthesis and purified according to methods known in the art. Any of a number of well-known procedures utilizing a variety of resins and reagents may be used to prepare the compounds of this invention.

The peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Routes of Administration. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

The peptides of this invention may be formulated or compounded into pharmaceutical compositions that include at least one peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of peptides of this invention administered to a patient will vary between fairly wide ranges depending upon the mode of administration, the formulation used, and the response desired.

Structure of Peptides of the Invention. This invention provides linear peptides of the following general formula:

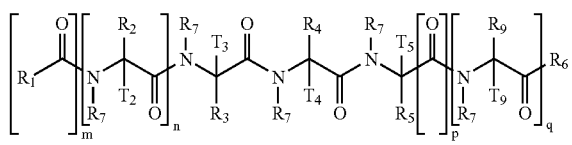

where:

$R_1$ is an aliphatic L- or D-amino acid, N-acylated L- or D-aliphatic amino acid or $R_8$;

$R_8$ is, in each instance, independently selected from the group consisting of linear or branched ($C_1$ to $C_{17}$) alkyl, aryl, heteroaryl, alkene, alkenyl, or aralkyl chains selected from the following:

$C_1$ to $C_{17}$ aliphatic linear chain or branched chain groups;

Acylated groups derived from $C_1$ to $C_{17}$ linear chain or branched chain aliphatics;

Omega amino and carboxylic derivatives of $C_1$ to $C_{17}$ aliphatic linear chain or branched chain groups; and Omega amino derivatives for acylated groups derived from $C_1$ to $C_{17}$ aliphatic linear chain or branched chained aliphatics.

$R_2$ and $R_3$ are each H, $CH_3$, an aromatic substituent aryl or heteroaryl side chain of a natural or synthetic L- or D-amino acid containing at least one aromatic moiety, wherein the ring(s) may additionally be functionalized by halogen, alkyl or aryl groups, and wherein the aromatic side group is preferably selected from the following side groups:

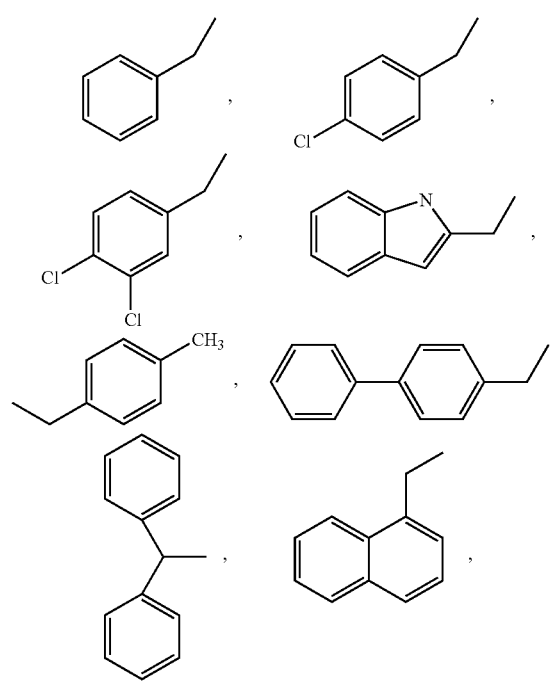

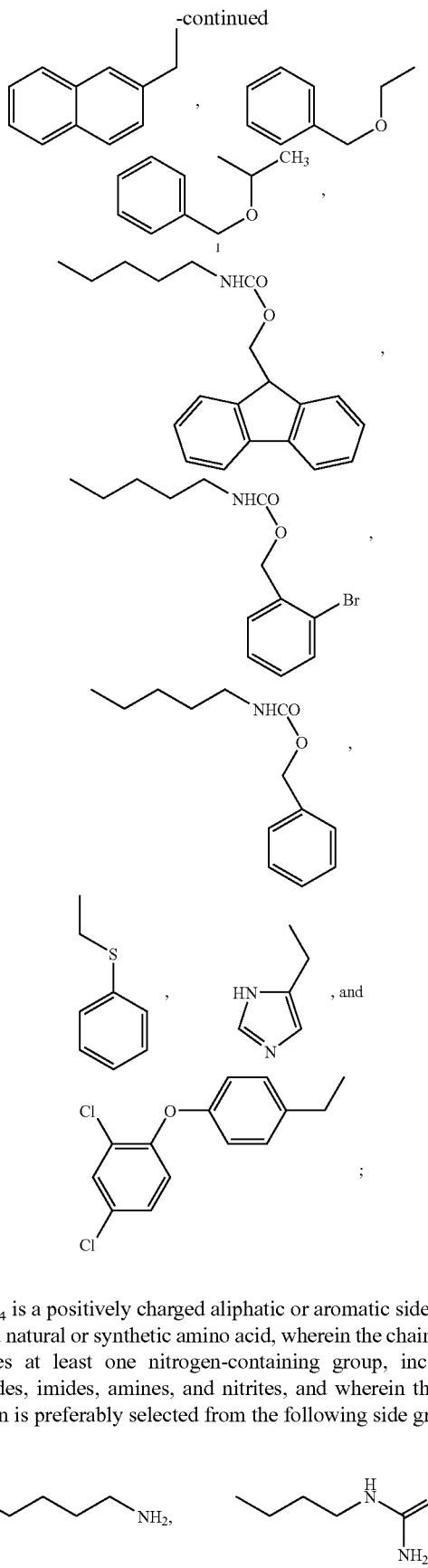

$R_4$ is a positively charged aliphatic or aromatic side chain for a natural or synthetic amino acid, wherein the chain comprises at least one nitrogen-containing group, including amides, imides, amines, and nitrites, and wherein the side chain is preferably selected from the following side groups:

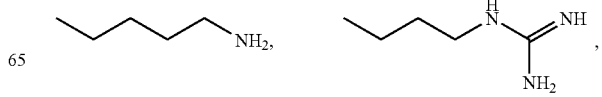

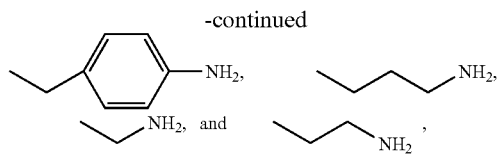

or is a neutral aliphatic side chain having hydrogen donors and/or acceptors, including but not limited to the following:

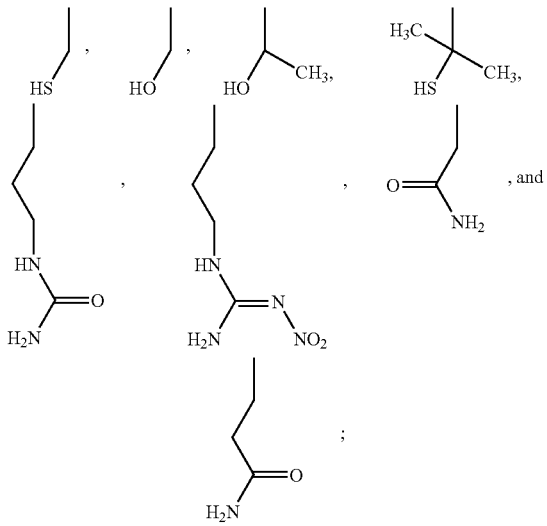

$R_5$ is H, $CH_3$, an aromatic substituent aryl or heteroaryl side chain of a natural or synthetic L- or D-amino acid containing at least one aromatic moiety, wherein the ring(s) may additionally be functionalized by halogen, alkyl or aryl groups, and wherein the aromatic side group is preferably selected from the side groups defined for $R_2$ and $R_3$, or a substituent alkyl or hydrogen bonding polar side chain of natural or synthetic L- or D-amino acids, wherein the side chain has a hydrogen donor or acceptor moiety;

$R_6$ is hydroxide, $NH_2$, or $NH$—$R_8$, where $R_8$ is preferably a short aliphatic $C_1$-$C_{17}$ chain, including an alkyl, aryl, heteroaryl, alkene, alkenyl or aralkyl;

$R_7$ is H, methyl, ethyl, propyl, butyl, or a similar higher linear or branched chain homolog, or a similar chain terminating in an amino group, benzyl, or similar aralkyl group;

$R_9$ is an amino acid side chain group, preferably selected from H, methyl, ethyl, propyl, butyl, or a similar higher linear or branched chain homolog, or a similar chain terminating in an amino group, benzyl, or similar aralkyl group;

m is normally 1 with the proviso that m may be 0 in which case this functionality is not present and the N-terminal group is an amine; and n is normally 1 with the proviso that n may be 0 in which case this amino add is not present;

p is normally 1 with the proviso that when p is 0 the chain terminates with the combination of $R_5$ and Ts and there is no q and no $R_6$; and q is normally 1 with the proviso that when q is 0 and p is 1 then the terminal group is $R_6$; and $T_2$, $T_3$ $T_4$, $T_5$, and $T_9$ are each H, $CH_3$, $C_2H_5$ or a benzyl group;

provided that one or more of the pairs $R_2$ and $T_2$, or $R_3$ and $T_3$, or $R_4$ and $T_4$, or $R_5$ and $T_5$, or $R_9$ and $T_9$ moieties may be joined together by additional carbon-carbon bonds to form a ring structure, and preferably a five-, six- or seven-membered ring structure; and further provided that one or more of $R_2$, $R_4$, $R_5$ or $R_9$ may be joined to the $R_7$ group that immediately precedes such $R_2$, $R_4$, $R_5$ or $R_9$ group by additional carbon-carbon bonds to form a ring structure, and preferably a five-, six- or seven-membered ring structure, thereby fixing such $R_2$, $R_4$, $R_5$ or $R_9$ group to the immediately preceding nitrogen atom.

In another embodiment, the invention provides cyclic peptides of the following general formula:

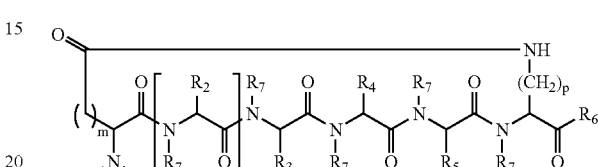

where:

$R_1$ is H, an aliphatic L- or D-amino acid, N-acylated L- or D-aliphatic amino acid or $R_8$;

$R_8$ is, in each instance, independently selected from the group consisting of linear or branched ($C_1$ to $C_{17}$) alkyl, aryl, heteroaryl, alkene, alkenyl, or aralkyl chains selected from the following:

$C_1$ to $C_{17}$ aliphatic linear chain or branched chain groups;

Acylated groups derived from $C_1$ to $C_{17}$ linear chain or branched chain aliphatics;

Omega amino derivatives of $C_1$ to $C_{17}$ aliphatic linear chain or branched chain groups; and Omega amino derivatives for acylated groups derived from $C_1$ to $C_{17}$ aliphatic linear chain or branched chain aliphatics.

$R_2$, $R_3$ and $R_5$ are each H, $CH_3$, an aromatic substituent aryl or heteroaryl side chain of a natural or synthetic L- or D-amino acid containing at least one aromatic moiety, wherein the ring(s) may additionally be functionalized by halogen, alkyl or aryl groups, and wherein the aromatic side group is preferably selected from the following side groups:

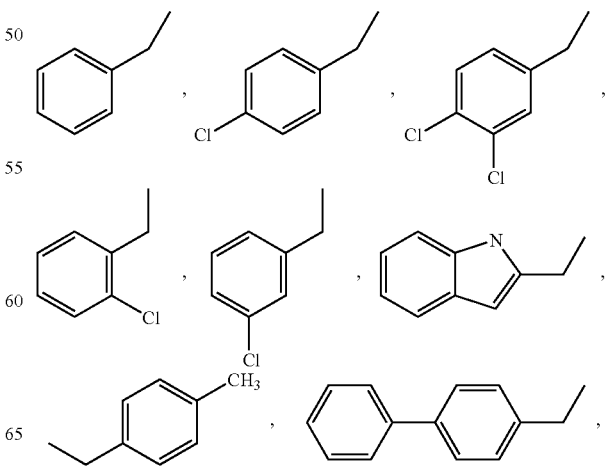

-continued

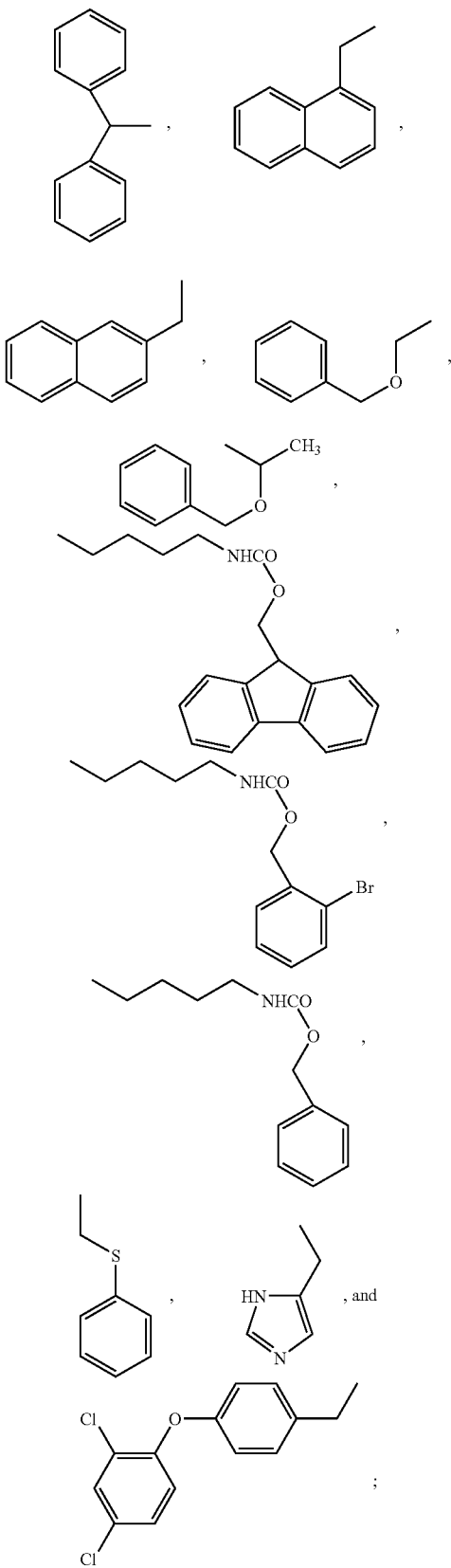

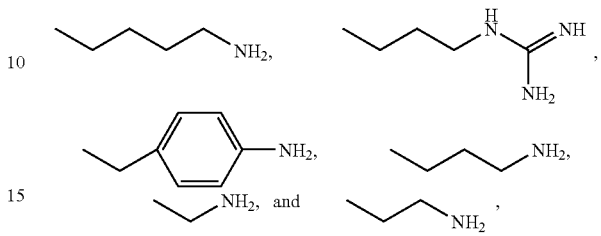

$R_4$ is a positively charged aliphatic or aromatic side chain of a natural or synthetic L- or D-amino acid, wherein the chain comprises at least one nitrogen-containing group, including amides, imides, amines, and nitriles, and wherein the side group is preferably selected from the following side groups:

or is a neutral aliphatic side chain having hydrogen donors and/or acceptors, including but not limited to the following:

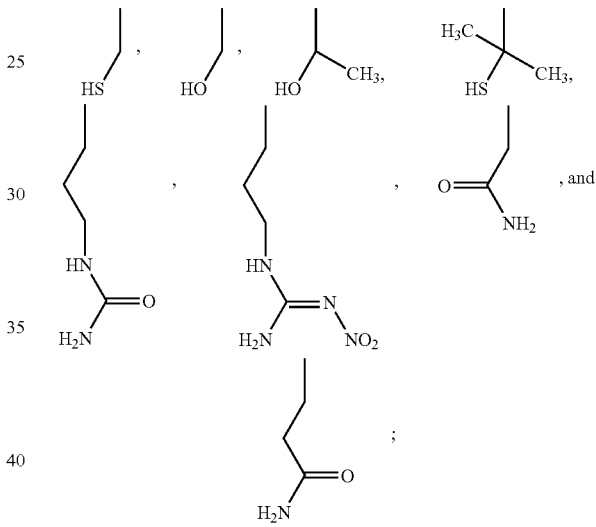

$R_6$ is hydroxide, $NH_2$, or $NH$—$R_8$, where $R_8$ is preferably a short aliphatic $C_1$-$C_{17}$ chain, including an alkyl, aryl, heteroaryl, alkene, alkenyl, or aralkyl;

$R_7$ is H, methyl, ethyl, propyl, butyl, or a similar higher linear or branched chain homolog, or a similar chain terminating in an amino group, benzyl, or similar aralkyl group;

m is 1 or 2;

n is normally 1 with the proviso that n may be 0 in which case this amino acid is not present; and p is 1 to 5.

Peptides of the Invention. Peptides of this invention were made using art conventional synthesis methods, and selected peptides were tested using a binding assay. Tables 1 and 2 set forth linear peptides of this invention and the results of competitive inhibition binding assays, while Tables 3 and 4 set forth cyclic peptides of this invention and the results of competitive inhibition binding assays.

In a preferred embodiment, the invention provides the peptide of the invention of the sequence 7'-amino-heptanoyl-Ser(Bzl)-D-Phe(4-Cl)-Arg-Trp-$NH_2$ having the following structure:

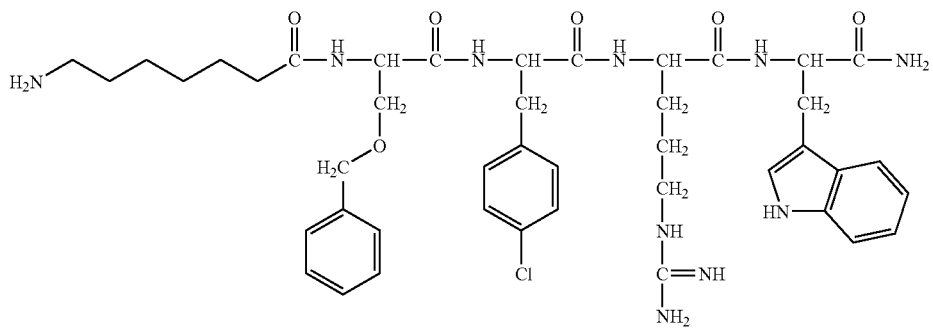

Competitive inhibition binding assays were conducted on peptides of the invention using membranes prepared from hMC3-R, hMC4-R, hMC5-R, and B-16 mouse melanoma cells (containing MC1-R) using 0.4 nM $^{125}$I-NDP-alpha-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test peptide of this invention, complexed to a rhenium metal ion as indicated, for determining its efficacy in inhibiting the binding of $^{125}$I-NDP-alpha-MSH to its receptor. Non-specific binding was measured by complete inhibition of binding of $^{125}$I-NDP-alpha-MSH in the assay with the presence of 1 μM alpha-MSH. Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM alpha-MSH. The cpm obtained in presence of test compounds were normalized with respect to 100% specific binding to determine the percent inhibition of $^{125}$I-NDP-alpha MSH binding. Each assay was conducted in triplicate and the actual mean values, as percent inhibition, are provided in Tables 1, 2, 3 and 4.

TABLE 1

Linear Peptides

| $S_1$ | $S_2$ | $S_3$ | $S_4$ | $S_5$ | MC1-R (B-16) | MC3-R | MC4-R | MC5-R |
|---|---|---|---|---|---|---|---|---|
| heptanoyl- | Ser(Bzl)- | D-Phe(4-Cl)— | Arg- | Trp-Cys-NH$_2$ | 27 | 76 | 97 | 99 |
| heptanoyl- | Ser(Bzl)- | D-Phe(4-Cl)— | Arg- | Trp-NH$_2$ | 60 | 98 | 97 | 97 |
| 7'-amino-heptanoyl- | D-Ala | D-Phe(4-Cl)— | Arg- | Trp-NH$_2$ | 30 | 0 | 31 | 1 |
| 2'-naphthylacetyl- | Val- | D-Phe(4-Cl)— | Arg- | Trp-NH$_2$ | 65 | 56 | 92 | 69 |
| 2'-naphthylacetyl- | Leu- | D-Phe(4-Cl)— | Arg- | Trp-NH$_2$ | 81 | 75 | 96 | 74 |
| 2'-naphthylacetyl- | Chg- | D-Phe(4-Cl)— | Arg- | Trp-NH$_2$ | 73 | 57 | 93 | 78 |
| 2'-naphthylacetyl- | Aib- | D-Phe(4-Cl)— | Arg- | Trp-NH$_2$ | 16 | 39 | 86 | 52 |
| 2'-naphthylacetyl | — | D-Phe(4-Cl)— | Arg- | Trp-NH$_2$ | 34 | 0 | 60 | 58 |
| 2'-naphthylacetyl- | Tle- | D-Phe(4-Cl)— | Arg- | Trp-NH$_2$ | 67 | 35 | 93 | 66 |
| 1-amino-1-cyclohexanecarbonyl | — | D-Phe(4-Cl)— | Arg- | Trp-NH$_2$ | 51 | 30 | 62 | 31 |
| 2'-naphthylacetyl- | 1-amino-1-cyclohexanecarbonyl- | D-Phe(4-Cl)— | Arg- | Trp-NH$_2$ | 25 | 35 | 92 | 63 |
| 2'-naphthylacetyl- | Ala- | D-Nal 2- | Arg- | Trp-NH$_2$ | 28 | 88 | 97 | 77 |
| 2'-naphthylacetyl- | D-Ala- | D-Nal 2- | Arg- | Trp-NH$_2$ | 1 | 34 | 77 | 44 |
| 2'-naphthylacetyl- | beta-Ala- | D-Nal 2- | Arg- | Trp-NH$_2$ | 1 | 58 | 89 | 59 |
| heptanoyl- | Ser(Bzl)- | D-Phe(4-Cl)— | Arg- | D-Trp-NH$_2$ | 76 | 83 | 98 | 86 |
| heptanoyl- | Ser(Bzl)- | D-Phe(4-Cl)— | Arg- | Trp-Val-NH$_2$ | 56 | 78 | 98 | 92 |
| heptanoyl- | Ser(Bzl)- | Arg- | D-Phe(4-Cl)— | Trp-NH$_2$ | 77 | 0 | 18 | 26 |
| heptanoyl- | Ser(Bzl)- | D-Phe- | Arg- | Trp-NH$_2$ | 75 | 52 | 88 | 38 |
| 7'-amino-heptanoyl- | Ser(Bzl)- | D-Phe(4-Cl)— | Arg- | D-Trp-NH$_2$ | 61 | 79 | 97 | 46 |
| 7'-amino-heptanoyl- | Ser(Bzl)- | D-Phe- | Arg- | Trp-NH$_2$ | 63 | 37 | 89 | 6 |
| 2'-naphthylacetyl- | Ala- | D-Phe(4-Cl)— | Arg- | D-Trp-NH$_2$ | 75 | 79 | 92 | 40 |
| 2'-naphthylacetyl- | Ala- | D-Phe(4-Cl)— | Arg- | Trp-NH$_2$ | 45 | 66 | 91 | 25 |
| 3'-chlorophenylacetyl- | Ala- | D-Phe(4-Cl)— | Arg- | Trp-NH$_2$ | 92 | 97 | 98 | 71 |
| 2'-naphthylacetyl- | Sar- | D-Phe(4-Cl)— | Arg- | Trp-NH$_2$ | 47 | 65 | 87 | 44 |
| heptanoyl- | Ser(Bzl)- | D-Phe(4-Cl)— | (Nlys)Gly- | Trp-NH$_2$ | 49 | 0 | 15 | 25 |
| 7'-amino-heptanoyl- | Ser(Bzl)- | D-Phe(4-Cl)— | Arg- | Trp-NH$_2$ | 33 | 94 | 99 | 73 |
| heptanoyl- | Ser(Bzl)- | D-Nal 2- | Arg- | Trp-NH$_2$ | 3 | 89 | 98 | 97 |
| 7'-amino-heptanoyl- | Ala- | D-Phe(4-Cl)— | Arg- | Trp-NH$_2$ | 58 | 75 | 88 | 15 |
| 7'-amino-heptanoyl- | beta-Ala- | D-Phe(4-Cl)— | Arg- | Trp-NH$_2$ | 25 | 0 | 22 | 2 |
| Ph—(CH$_2$)$_2$NH— | CO(CH$_2$)$_2$CO— | D-Phe(4-Cl)— | Arg- | Trp-NH$_2$ | 67 | 82 | 90 | 54 |
| 4'-bromophenyl-acetyl- | Ala- | D-Phe(4-Cl)— | Arg- | Trp-NH$_2$ | 29 | 97 | 95 | 65 |
| 3',4'-dichlorophenyl-acetyl- | Ala- | D-Phe(4-Cl)— | Arg- | Trp-NH$_2$ | 40 | 100 | 98 | 81 |
| 2',4'-dichlorophenyl-acetyl- | Ala- | D-Phe(4-Cl)— | Arg- | Trp-NH$_2$ | 0 | 85 | 92 | 38 |
| 4'-biphenyl-acetyl- | Ala- | D-Phe(4-Cl)— | Arg- | Trp-NH$_2$ | 0 | 54 | 88 | 37 |

TABLE 1-continued

Linear Peptides

| S₁ | S₂ | S₃ | S₄ | S₅ | MC1-R (B-16) | MC3-R | MC4-R | MC5-R |
|---|---|---|---|---|---|---|---|---|
| 2'-naphthoyl- | Inp- | D-Phe(4-Cl)— | Arg- | Trp-NH₂ | 10 | 19 | 59 | 19 |
| 2'-naphthylacetyl- | Inp- | D-Phe(4-Cl)— | Arg- | Trp-NH₂ | 2 | 15 | 58 | 36 |
| 4'-phenylbutylamino-carbonyl | — | D-Phe(4-Cl)— | Arg- | Trp-NH₂ | 0 | 0 | 45 | 49 |
| 3'-phenylpropylamino-carbonyl | — | D-Phe(4-Cl)— | Arg- | Trp-NH₂ | 0 | 3 | 60 | 51 |
| 4'phenylbutyryl- | Ala- | D-Phe(4-Cl)— | Arg- | Trp-NH₂ | 20 | 79 | 94 | 46 |
| 2'-naphthoyl- | Pip- | D-Phe(4-Cl)— | Arg- | Trp-NH₂ | 5 | 12 | 46 | 32 |
| 2'-naphthylacetyl- | Pip- | D-Phe(4-Cl)— | Arg- | Trp-NH₂ | 12 | 54 | 77 | 55 |
| heptanoyl- | Ser(Bzl)- | D-Phe(4-Cl)— | Lys- | Trp-NH₂ | 0 | 35 | 85 | 48 |
| heptanoyl- | Ser(Bzl)- | D-Phe(4-Cl)— | Arg- | Phe-NH₂ | 0 | 31 | 63 | 32 |
| heptanoyl- | Ser(Bzl)- | D-Phe(4-Cl)— | Arg- | 3'-Pya-NH₂ | 0 | 0 | 24 | 19 |
| heptanoyl- | Ser(Bzl)- | D-Phe(4-Cl)— | Trp- | 4'-amino-butylamide | 0 | 0 | 17 | 30 |
| heptanoyl- | Ser(Bzl)- | D-Phe(4-Cl)— | Arg- | MeTrp-NH₂ | 71 | 92 | 99 | 85 |
| heptanoyl- | MeThr(Bzl)- | D-Phe(4-Cl)— | Arg- | Trp-NH₂ | 4 | 18 | 78 | 39 |
| heptanoyl- | Thr(Bzl)- | D-Phe(4-Cl)— | Arg- | Trp-NH₂ | 28 | 39 | 91 | 65 |
| heptanoyl- | D-Thr(Bzl)- | D-Phe(4-Cl)— | Arg- | Trp-NH₂ | 11 | 4 | 19 | 31 |
| heptanoyl- | Ser(Bzl)- | D-Phe(4-Cl)— | Arg- | beta-Ala-Trp-NH₂ | 20 | 13 | 25 | 44 |
| 2'-bromophenyl-acetyl- | Ala- | D-Phe(4-Cl)— | Arg- | Trp-NH₂ | 40 | 81 | 93 | 36 |
| 3'-bromophenyl-acetyl- | Ala- | D-Phe(4-Cl)— | Arg- | Trp-NH₂ | 86 | 97 | 98 | 90 |
| 4'-CF₃phenyl-acetyl- | Ala- | D-Phe(4-Cl)— | Arg- | Trp-NH₂ | 70 | 98 | 98 | 69 |
| 3'-CF₃phenyl-acetyl- | Ala- | D-Phe(4-Cl)— | Arg- | Trp-NH₂ | 96 | 101 | 100 | 96 |
| 2'-CF₃phenyl-acetyl- | Ala- | D-Phe(4-Cl)— | Arg- | Trp-NH₂ | 41 | 85 | 92 | 35 |
| 3',5'-CF₃phenylacetyl- | Ala- | D-Phe(4-Cl)— | Arg- | Trp-NH₂ | 89 | 95 | 98 | 92 |
| 2',5'-CF₃phenylacetyl- | Ala- | D-Phe(4-Cl)— | Arg- | Trp-NH₂ | 75 | 79 | 95 | 75 |
| 4'-Mephenyl-acetyl- | Ala- | D-Phe(4-Cl)— | Arg- | Trp-NH₂ | 56 | 93 | 96 | 61 |
| 3'-Mephenyl-acetyl- | Ala- | D-Phe(4-Cl)— | Arg- | Trp-NH₂ | 77 | 94 | 96 | 74 |
| 2'-Mephenyl-acetyl- | Ala- | D-Phe(4-Cl)— | Arg- | Trp-NH₂ | 44 | 86 | 93 | 50 |
| heptanoyl- | Ser(Bzl)- | D-Phe(4-Cl)— | Dpr(beta-Ala)- | Trp-NH₂ | 5 | 21 | 65 | 28 |
| 7'-amino-heptanoyl- | Ser(Bzl)- | D-Phe(4-Cl)— | Arg- | Trp-OH | 35 | 34 | 67 | 25 |
| 7'-amino-heptanoyl- | Ser(Bzl)- | D-Phe(4-Cl)— | Arg- | MeTrp-NH₂ | 76 | 95 | 99 | 86 |
| beta-Ala- | Ser(Bzl)- | D-Phe(4-Cl)— | Arg- | Trp-NH₂ | 66 | 89 | 99 | 86 |
| 4-aminoButyl- | Ser(Bzl)- | D-Phe(4-Cl)— | Arg- | Trp-NH₂ | 63 | 90 | 99 | 78 |
| 5-aminoValeryl- | Ser(Bzl)- | D-Phe(4-Cl)— | Arg- | Trp-NH₂ | 57 | 88 | 98 | 71 |
| 6-aminoCaproyl- | Ser(Bzl)- | D-Phe(4-Cl)— | Arg- | Trp-NH₂ | 69 | 91 | 99 | 75 |
| aminoTranexamyl- | Ser(Bzl)- | D-Phe(4-Cl)— | Arg- | Trp-NH₂ | 56 | 90 | 98 | 74 |
| Cmpi- | Ser(Bzl)- | D-Phe(4-Cl)— | Arg- | Trp-NH₂ | 66 | 88 | 99 | 79 |
| 7'-amino-heptanoyl- | Thr(Bzl)- | D-Phe(4-Cl)— | Arg- | Trp-NH₂ | 38 | 48 | 94 | 68 |
| 7'-amino-heptanoyl- | Ser(Bzl)- | D-Phe(4-Cl)— | Arg- | D-Nal 1-NH₂ | 25 | 24 | 71 | 36 |
| 7'-amino-heptanoyl- | Ser(Bzl)- | D-Phe(4-Cl)— | Arg- | Nal 1-NH₂ | 21 | 60 | 95 | 49 |
| 7'-amino-heptanoyl- | Ser(Bzl)- | D-Phe(4-Cl)— | Arg- | D-Tic-NH₂ | 3 | 0 | 6 | 10 |
| 7'-amino-heptanoyl- | Ser(Bzl)- | D-Phe(4-Cl)— | Arg- | Tic-NH₂ | 45 | 0 | 19 | 20 |
| 7'-amino-heptanoyl- | Ser(Bzl)- | D-Phe(4-Cl)— | Arg- | D-Nal 2-NH₂ | 50 | 93 | 99 | 78 |
| 7'-amino-heptanoyl- | Ser(Bzl)- | D-Phe(4-Cl)— | Arg- | Nal 2-NH₂ | 64 | 95 | 100 | 90 |
| 7'-amino-heptanoyl- | Ser(Bzl)- | D-Phe(4-Cl)— | D-Arg- | Trp-NH₂ | 18 | 1 | 12 | 27 |
| 7'-amino-heptanoyl- | Ser(Bzl)- | D-Phe(4-Cl)— | Arg- | 1-aminoindane-1-caboxyl-NH₂ | 21 | 0 | 8 | 12 |
| 7'-amino-heptanoyl- | Ser(Bzl)- | D-Phe(4-Cl)— | Arg- | Aic-NH₂ | 3 | 0 | 33 | 13 |
| 7'-amino-heptanoyl- | Ser(Bzl)- | D-Phe(4-Cl)— | Arg- | Atc-NH₂ | 7 | 34 | 84 | 27 |
| 7'-amino-heptanoyl- | Ser(Bzl)- | D-Phe(4-Cl)— | Arg- | Tpi-NH₂ | 18 | 50 | 80 | 37 |
| 7'-amino-heptanoyl- | Ser(Bzl)- | D-Phe(4-Cl)— | Arg- | D-Tpi-NH₂ | 16 | 7 | 51 | 29 |
| 7'-amino-heptanoyl- | Ser(Bzl)- | D-Phe(4-Cl)— | Arg- | Tiq-NH₂ | 8 | 0 | 8 | 24 |
| 7'-amino-heptanoyl- | Ser(Bzl)- | D-Phe(4-Cl)— | Arg- | D-Tiq-NH₂ | 8 | 0 | 2 | 23 |
| 7'-amino-heptanoyl- | Ser(Bzl)- | D-Phe(4-Cl)— | Lys- | Trp-NH₂ | 22 | 51 | 83 | 33 |
| 7'-amino-heptanoyl- | Ser(Bzl)- | D-Phe(4-Cl)— | homoLys- | Trp-NH₂ | 27 | 33 | 71 | 8 |
| 7'-amino-heptanoyl- | Ser(Bzl)- | D-Phe(4-Cl)— | alpha-(N-amidino-4'-piperidine)Gly | Trp-NH₂ | 3 | 8 | 26 | 16 |
| 7'-amino-heptanoyl- | Ser(Bzl)- | D-Phe(4-Cl)— | (4'-guanidino)Gly | Trp-NH₂ | 3 | 8 | 22 | 27 |
| 7'-amino-heptanoyl- | Ser(Bzl)- | D-Phe(4-Cl)— | D-(4-guanidino)Phe | Trp-NH₂ | 0 | 9 | 0 | 8 |
| 7'-amino-heptanoyl- | Ser(Bzl)- | D-Phe(4-Cl)— | beta-(N-amidino-4'-peperidine)Ala | Trp-NH₂ | 0 | 13 | 56 | 8 |
| 7'-amino-heptanoyl- | Ser(Bzl)- | D-Phe(4-Cl)— | Arg- | Tryptamide | 36 | 74 | 97 | 54 |
| 7'-amino-heptanoyl- | Ser(Bzl)- | D-Phe(4-Cl)— | Arg- | NMe-Tryptamide | 56 | 55 | 96 | 66 |
| 7'-amino-heptanoyl- | Ser(Bzl)- | D-Phe(4-Cl)— | Arg- | alpha-Me-Tryptamide | 61 | 84 | 99 | 71 |
| 7'-amino-heptanoyl- | Ser(Bzl)- | D-Phe(4-Cl)— | Arg- | 2'-(4''-methylphenyl)ethyl amide | 38 | 67 | 90 | 43 |

TABLE 1-continued

Linear Peptides

| S₁ | S₂ | S₃ | S₄ | S₅ | MC1-R (B-16) | MC3-R | MC4-R | MC5-R |
|---|---|---|---|---|---|---|---|---|
| 7'-amino-heptanoyl- | Ser(Bzl)- | D-Phe(4-Cl)— | Arg- | 3',4'-Cl₂phenylmethylamide | 8 | 32 | 41 | 28 |
| 7'-amino-heptanoyl- | Ser(Bzl)- | D-Phe(4-Cl)— | Arg- | 1'-aminoindan | 28 | 26 | 57 | 0 |
| 3',4'-Cl₂phenylacetyl- | Ala- | D-Phe- | Arg- | Trp-NH₂ | 75 | 80 | 83 | 38 |
| 3',4'-Cl₂phenylacetyl- | Ala- | D-Phe(3,4-F₂)— | Arg- | Trp-NH₂ | 72 | 92 | 93 | 51 |
| 3',4'-Cl₂phenylacetyl- | Ala- | D-Val- | Arg- | Trp-NH₂ | 0 | 0 | 2 | 0 |
| 3',4'-Cl₂phenylacetyl- | Ala- | D-Phe(4-Cl)- | Lys- | Trp-NH₂ | 45 | 84 | 85 | 52 |
| 3',4'-Cl₂phenylacetyl- | Ala- | D-Phe(4-Cl)— | Arg- | 3'-phenylpropylamide | 0 | 44 | 39 | 16 |
| 3',4'-Cl₂phenylacetyl- | Ala- | D-Phe(4-Cl)— | Arg- | 2'-(4"-methylphenyl)ethylamide | 33 | 77 | 79 | -6 |
| 3'-CF₃phenylacetyl- | Ala- | D-Phe- | Arg- | Trp-NH₂ | 85 | 55 | 72 | 41 |
| 3'-CF₃phenylacetyl- | Ala- | D-Phe(3,4-F₂)— | Arg- | Trp-NH₂ | 87 | 77 | 90 | 71 |
| 3'-CF₃phenylacetyl- | Ala- | D-Val- | Arg- | Trp-NH₂ | 2 | 0 | 0 | 1 |
| 3'-CF₃phenylacetyl- | Ala- | D-Phe(4-Cl)- | Lys- | Trp-NH₂ | 75 | 64 | 84 | 67 |
| 7'-amino-heptanoyl- | Ser(Bzl)- | D-Phe(4-Cl)— | Arg- | Disc-NH₂ | 0 | 0 | 0 | 18 |
| 7'-amino-heptanoyl- | Ser(Bzl)- | D-Phe(4-Cl)— | Arg- | 3'-phenylpropylamide | 14 | 12 | 30 | 34 |
| 3'-CF₃phenylacetyl- | Ala- | D-Phe(4-Cl)— | Arg- | Tryptamide | 87 | 94 | 98 | 89 |
| 3'-CF₃phenylacetyl- | Ala- | D-Phe(4-Cl)— | Arg- | 2'-(4"-methylphenyl)ethylamide | 59 | 64 | 75 | 27 |
| 7'-amino-heptanoyl- | Ser(Bzl)- | D-Phe(4-Cl)— | Arg- | 2',4'-dichlorobenzylamide | 9 | 5 | 20 | -6 |
| 7'-amino-heptanoyl- | Ser(Bzl)- | D-Phe(4-Cl) | Arg- | 3'-(1H-imidazol)propylamide | 2 | 7 | 4 | 16 |
| 7'-amino-heptanoyl- | Ser(Bzl)- | D-Phe(4-Cl) | Arg- | 4-phenyl-piperidine-4-carbonamide | 5 | 2 | 13 | 25 |
| 7'-amino-heptanoyl- | Ser(Bzl)- | D-Phe(4-Cl) | Arg- | 3-phenyl-1-propylamide | 11 | 23 | 49 | 28 |
| 7'-amino-heptanoyl- | Ser(Bzl)- | D-Phe(4-Cl)— | Arg- | 2,4-dichlorophenethylamide | 19 | 43 | 86 | 54 |
| 7'-amino-heptanoyl- | Ser(Bzl)- | D-Phe(4-Cl)— | homo-Ala-4-pip(N-amidino)- | Trp-NH₂ | 4 | 8 | 34 | 17 |
| 7'-amino-heptanoyl- | Ser(Bzl)- | D-Phe(4-Cl)— | Arg- | S-(−)-1-(2-Naphthyl)ethylamide | 3 | 1 | 59 | 33 |
| 7-amino-heptanoyl- | Ser(Bzl)- | D-Phe(4-Cl)— | Arg- | S-(−)-1-(1-Naphthyl)ethylamide | 46 | 85 | 98 | 64 |
| 7'-amino-heptanoyl- | Ser(Bzl)- | D-Phe(4-Cl)— | Arg- | 2'-methylbenzylamide | 10 | 15 | 34 | 44 |
| 7'-amino-heptanoyl- | Ser(Bzl)- | D-Phe(4-Cl)— | Arg- | 3'-methylbenzylamide | 18 | 11 | 35 | 38 |
| 7'-amino-heptanoyl- | Ser(Bzl)- | D-Phe(4-Cl)— | Arg- | 4'-methylbenzylamide | 7 | 22 | 42 | 44 |
| 7'-amino-heptanoyl- | Ser(Bzl)- | D-Phe(4-Cl)— | Arg- | 2',2'-diphenylethylamide | 4 | 11 | 24 | 34 |
| 7'-amino-heptanoyl- | Ser(Bzl)- | D-Phe(4-Cl)— | Arg- | 4'-(2"-pyridyl)piperazineamide | 12 | 7 | 30 | 30 |
| 7'-amino-heptanoyl- | Ser(Bzl)- | D-Phe(4-Cl)— | Arg- | N-benzylmethylamide | 17 | 12 | 34 | 33 |
| 7'-amino-heptanoyl- | Ser(Bzl)- | D-Phe(4-Cl)— | Arg- | 1',2'-diphenylethylamide | 14 | 42 | 92 | 52 |
| 7'-amino-heptanoyl- | Ser(Bzl)- | D-Phe(4-Cl)— | Arg- | Histamide | 4 | 0 | 9 | -2 |
| 7'-amino-heptanoyl- | Ser(Bzl)- | D-Phe(4-Cl)— | Arg- | R-(+)-1-(2-Naphthyl)ethylamide | 3 | 0 | 21 | 26 |
| 7'-amino-heptanoyl- | Ser(Bzl)- | D-Nal 2- | Arg- | Trp-NH₂ | 4 | 93 | 99 | 82 |
| 7'-amino-heptanoyl- | Ala- | D-Nal 2- | Arg- | Trp-NH₂ | 0 | 57 | 84 | 15 |
| 7'-amino-heptanoyl- | D-Ala- | D-Nal 2- | Arg- | Trp-NH₂ | 0 | 0 | 19 | 0 |
|  | Ser(Bzl)- | D-Nal 2- | Arg- | Trp-NH₂ | 10 | 35 | 92 | 64 |
|  | Ser(Bzl)- | D-Nal 2- | Arg- | D-Trp-NH₂ | 21 | 51 | 90 | 74 |
| 7'-amino-heptanoyl- | Ser(Bzl)- | D-Nal 2- | Arg- | D-Trp-NH₂ | -8 | 86 | 100 | 82 |
| 2'-Naphthylacetyl- | Ala- | D-Phe(4-Cl)— | Arg- | Trp-Asp-NH₂ | 65 | 96 | 98 | 68 |
| 7'-amino-heptanoyl- | Ser(Bzl)- | D-Phe(4-Cl)— | Arg- | Trp-Asp-NH₂ | 35 | 73 | 98 | 48 |
| 7'-amino-heptanoyl- | Ser(Bzl)- | D-Phe(4-Cl)— | Arg- | Trp-Asp-Phe-NH₂ | 34 | 37 | 100 | 54 |
| 7'-amino-heptanoyl- | Ser(Bzl)- | D-Phe(4-Cl)— | Arg- | Asp-Trp-NH₂ | 59 | 0 | 12 | 10 |
| 7'-amino-heptanoyl- | Ser(Bzl)- | D-Phe(4-Cl)— | Arg- | Ala-Trp-NH₂ | 60 | 10 | 31 | 42 |
| 7'-amino-heptanoyl- | Ser(Bzl)- | D-Phe(4-Cl)— | Arg- | Trp-Ala-NH₂ | 60 | 93 | 100 | 79 |
| 7'-amino-heptanoyl- | Ser(Bzl)- | D-Phe(4-Cl)— | Arg- | phenethylamide | 25 | 50 | 75 | 50 |
| 7'-amino-heptanoyl- | Ser(Bzl)- | D-Phe(4-Cl)— | Arg- | Trp-Asp-OH | 4 | 16 | 67 | 3 |
| 7'-amino-heptanoyl- | Ser- | D-Phe(4-Cl)— | Arg- | Trp-NH₂ | 19 | 61 | 69 | 11 |
| 7'-amino-heptanoyl- | Ser(Bzl)- | Phe(4-Cl)— | Arg- | Trp-NH₂ (SEQ ID NO: 2) | 4 | 10 | 0 | 52 |
|  | Ser(Bzl)- | D-Phe(4-Cl)— | Arg- | Trp-NH₂ | 27 | 65 | 86 | 65 |

TABLE 2

Linear Peptides

| S₁ | S₂ | S₃ | S₄ | S₅ | Conc. µM | MC1-R (B-16) | MC3-R | MC4-R | MC5-R |
|---|---|---|---|---|---|---|---|---|---|
| Ac-Nle-Asp- | His- | D-Phe- | Orn- | Trp-Lys[N-epsilon (=C(NMe₂)₂)]—NH₂ | 10 | 102 | | 72 | |
| Ac-Nle-Asp- | His- | D-Phe- | Cit- | Trp-Lys[N-epsilon (=C(NMe₂)₂)]—NH₂ | 1 | 87 | | 62 | |
| Ac-Nle-Asp- | His- | His- | Arg- | Trp-Lys-NH₂ (SEQ ID NO: 3) | 1 | 34 | | 28 | |
| Ac- | His- | Phe- | Cys- | Trp-NH₂ (SEQ ID NO: 4) | 10 | 54 | | 29 | |
| Ac- | His- | D-Phe- | Cys- | Trp-NH₂ | 10 | 91 | | 8 | |
| Ac-Nle-Ala- | His- | D-Phe- | Cys- | Trp-NH₂ | 1 | 65 | | | |
| Ac-Nle-Ala- | His- | D-Phe- | Arg- | Cys-Trp-NH₂ | 1 | 101 | | 57 | |
| Ac-Nle-Ala-His- | His- | D-Phe- | Arg- | Cys-Trp-NH₂ | 0.1 | 95 | | 43 | |
| heptanoyl- | His- | D-Phe- | Arg- | Cys-Trp-NH₂ | 1 | 97 | | 55 | |
| heptanoyl- | His- | D-Phe- | Arg- | Cys-Trp-NH₂ | 0.1 | 75 | | 36 | |
| HOOC-(CH₂)₅-CO- | His- | D-Phe- | Arg- | Cys-Trp-NH₂ | 1 | 95 | | 29 | |
| HOOC-(CH₂)₅-CO- | His- | D-Phe- | Arg- | Cys-Trp-NH₂ | 0.1 | 76 | | 1 | |
| NH₂-(CH₂)₅-CO- | His- | D-Phe- | Arg- | Cys-Trp-NH₂ | 1 | 96 | | 56 | |
| NH₂-(CH₂)₅-CO- | His- | D-Phe- | Arg- | Cys-Trp-NH₂ | 0.1 | 87 | | 7 | |
| Ac-Nle-Asp- | His- | D-Phe- | Cit- | Trp-Lys-NH₂ | 1 | 90 | | 92 | |
| Ac-Nle-Asp- | His- | D-Phe- | Cit- | Trp-Lys-NH₂ | 0.1 | 55 | | 28 | |
| Ac-Nle-Asp- | His- | D-Phe- | Cit- | Trp-Lys-NH₂ | 0.01 | 33 | | 24 | |
| Ac-Nle-Asp- | His- | D-Phe- | Arg- | Trp-Lys-OH | 1 | 90 | 18 | 53 | 15 |
| Ac-Nle-Ala- | His- | D-Phe- | Arg- | Trp-NH₂ | 1 | 101 | 84 | 95 | 77 |
| Ac-Nle-Ala- | His- | D-Phe- | Arg- | Trp-Cys-NH₂ | 1 | 97 | 58 | 93 | 100 |
| heptanoyl- | Ser(Bzl)- | D-Nal 2- | Arg- | Trp-NH₂ | 1 | 3 | 89 | 98 | 97 |
| heptanoyl- | Ser(Bzl)- | D-Nal 2- | Arg- | Trp-Cys-NH₂ | 1 | 2 | 72 | 97 | 101 |
| 2-Naphthylacetyl- | Ser(Bzl)- | D-Phe(4-Cl)— | Arg- | Trp-NH₂ | 1 | 15 | 93 | 98 | 71 |
| 2-Naphthylacetyl- | D-Ala- | D-Phe(4-Cl)— | Arg- | Trp-NH₂ | 1 | 5 | 18 | 56 | 26 |
| 4'-chlorophenylacetyl- | Ala- | D-Phe(4-Cl)— | Arg- | Trp-NH₂ | 1 | 62 | 90 | 95 | 68 |
| 2'-chlorophenylacetyl- | Ala- | D-Phe(4-Cl)— | Arg- | Trp-NH₂ | 1 | 3 | 48 | 87 | 28 |
| Ph-(CH₂)₂NH- | CO(CH₂)₂CO— | D-Phe(4-Cl)— | Arg- | Trp-NH₂ | 1 | 67 | 82 | 90 | 54 |
| Ph-(CH₂)₂NH-CO | — | D-Phe(4-Cl)— | Arg- | Trp-NH₂ | 1 | 1 | 11 | 63 | 27 |

TABLE 3

Cyclic Peptides

| S₁ | S₂ | S₃ | S₄ | S₅ | MC1-R (B-16) | MC3-R | MC4-R | MC5-R |
|---|---|---|---|---|---|---|---|---|
| Cyclo1,6 [2-Naphthylacetyl-Asp- | Ser(Bzl)- | D-Phe(2-Cl)— | Arg- | Trp-Lys-NH₂] | 16 | 87 | 97 | 44 |
| Cyclo1,6 [heptanoyl-Asp- | His- | D-Phe(2-Cl)— | Arg- | Trp-Lys-NH₂] | 99 | 80 | 100 | 98 |
| Cyclo1,6 [2-Naphthylacetyl-Asp- | His- | D-Nal 2- | Arg- | Trp-Lys-NH₂] | 89 | 85 | 100 | 94 |
| Cyclo1,6 [heptanoyl-Asp- | Ser(Bzl)- | D-Phe(2-Cl)— | Arg- | Trp-Lys-NH₂] | 86 | 84 | 99 | 98 |

TABLE 4

Cyclic Peptides

| S₁ | S₂ | S₃ | S₄ | S₅ | Conc. µM | MC1-R (B-16) | MC3-R | MC4-R | MC5-R |
|---|---|---|---|---|---|---|---|---|---|
| Cyclo2,7 [Ac-Nle-Asp- | His- | D-Phe(3,4-diCl)— | Arg- | Trp-Lys-NH₂] | 1 | 98 | | 103 | |
| Cyclo1,6 [heptanoyl-Asp- | Ser(Bzl)- | D-Phe(3-Cl)— | Arg- | D-Nal 2-Lys-NH₂] | 1 | 85 | | 100 | |
| Cyclo1,6 [heptanoyl-Asp- | Ser(Bzl)- | D-Phe(3-Cl)— | Arg- | D-Nal 2-Lys-NH₂] | 0.1 | 48 | | 97 | |
| Cyclo1,6 [heptanoyl-Asp- | Ser(Bzl)- | D-Phe(3-Cl)— | Arg- | D-Nal 2-Lys-NH₂] | 0.01 | 26 | | 74 | |
| Cyclo1,6 [heptanoyl-Asp- | Nal 2- | D-Phe(3-Cl)— | Arg- | Ser(Bzl)-Lys-NH₂] | 1 | 51 | | 82 | |
| Cyclo2,7 [Ac-Nle-Asp- | His- | D-Phe- | Cit- | Trp-Lys-NH₂] | 1 | 95 | | 100 | |
| Cyclo2,7 [Ac-Nle-Asp- | His- | D-Phe- | Cit- | Trp-Lys-NH₂] | 0.1 | 88 | | 95 | |
| Cyclo2,7 [Ac-Nle-Asp- | His- | D-Phe- | Cit- | Trp-Lys-NH₂] | 0.01 | 70 | | 72 | |
| Cyclo2,7 [Ac-Nle-Asp- | His- | D-Phe- | Orn- | Trp-Lys-NH₂] | 0.1 | 75 | | 60 | |
| Cyclo2,7 [Ac-Nle-Asp- | His- | D-Phe- | Orn- | Trp-Lys-NH₂] | 0.01 | 53 | | 17 | |
| Cyclo2,7 [Ac-Nle-Asp- | His- | Phe- | Arg- | Trp-Lys-NH₂] | 0.1 | 74 | | 60 | |
| Cyclo2,7 [Ac-Nle-Asp- | His- | Phe- | Arg- | Trp-Lys-NH₂] | 0.01 | 50 | | 24 | |
| Cyclo2,7 [Ac-Nle-Asp- | His- | D-Phe- | Ser- | Trp-Lys-NH₂] | 0.1 | 60 | | 20 | |
| Cyclo2,7 [Ac-Nle-Asp- | His- | D-Phe- | Ser- | Trp-Lys-NH₂] | 0.01 | 41 | | 21 | |

TABLE 4-continued

Cyclic Peptides

| S1 | S2 | S3 | S4 | S5 | Conc. μM | MC1-R (B-16) | MC3-R | MC4-R | MC5-R |
|---|---|---|---|---|---|---|---|---|---|
| Cyclo2,7 [Ac-Nle-Asp- | His- | D-Phe- | Lys- | Trp-Lys-NH2] | 1 | 100 | | 93 | |
| Cyclo2,7 [Ac-Nle-Asp- | His- | D-Phe- | Lys- | Trp-Lys-NH2] | 0.1 | 98 | | 93 | |
| Cyclo2,7 [Ac-Nle-Asp- | His- | D-Phe- | Lys- | Trp-Lys-NH2] | 0.01 | 88 | | 51 | |
| Cyclo2,7 [Ac-Nle-Asp- | His- | MePhe- | Arg- | Trp-Lys-NH2] | 1 | 32 | | 22 | |
| Cyclo2,7 [Ac-Nle-Asp- | His- | D-MePhe | Arg- | Trp-Lys-NH2] | 0.1 | 1 | | 46 | |
| Cyclo2,7 [Ac-Nle-Asp- | His- | D-MePhe- | Arg- | Trp-Lys-NH2] | 1 | 44 | | 70 | |
| Cyclo2,7 [Ac-Nle-Asp- | His- | D-Phe- | MeArg- | Trp-Lys-NH2] | 1 | 100 | | 100 | |
| Cyclo2,7 [Ac-Nle-Asp- | His- | D-Phe- | MeArg- | Trp-Lys-NH2] | 0.1 | 100 | | 92 | |
| Cyclo2,7 [Ac-Nle-Asp- | His- | D-Phe- | MeArg- | Trp-Lys-NH2] | 0.01 | 95 | | 66 | |
| Cyclo2,7 [Ac-Nle-Asp- | His- | D-Phe- | MeArg- | Trp-Lys-NH2] | 0.001 | 69 | | 38 | |
| Cyclo2,7 [Ac-Nle-Asp- | His- | D-Phe- | MeArg- | Trp-Lys-NH2] | 1 | 97 | | 96 | |
| Cyclo2,7 [Ac-Nle-Asp- | His- | D-Phe- | Arg- | MeTrp-Lys-NH2] | 1 | 99 | | 100 | |
| Cyclo2,7 [Ac-Nle-Asp- | His- | D-Phe- | Arg- | MeTrp-Lys-NH2] | 0.1 | 94 | | 93 | |
| Cyclo2,7 [Ac-Nle-Asp- | His- | D-Phe- | Arg- | MeTrp-Lys-NH2] | 0.01 | 66 | | 60 | |
| Cyclo2,7 [Ac-Nle-Asp- | His- | D-Phe- | Arg- | MeTrp-Lys-NH2] | 0.001 | 35 | | 41 | |
| Cyclo2,7 [Ac-Nle-Asp- | His- | D-Tpi- | Arg- | Trp-Lys-NH2] | 1 | 53 | | 81 | |
| Cyclo2,7 [Ac-Nle-Asp- | His- | D-MePhe- | Arg- | Trp-Orn-NH2] | 1 | 52 | | 60 | |
| Cyclo2,7 [Ac-Nle-Glu- | His- | D-MePhe- | Arg- | Trp-Lys-NH2] | 1 | 59 | | 43 | |
| Cyclo2,7 [Ac-Nle-Asp- | His- | D-Tic- | Arg- | Trp-Lys-NH2] | 1 | 28 | | 31 | |
| Cyclo2,7 [Ac-Nle-Asp- | His- | D-MePhe- | Arg- | MeTrp-Lys-NH2] | 1 | 62 | | 85 | |
| Cyclo2,7 [Ac-Nle-Asp- | Arg- | D-Nal 2'- | Arg- | Trp-Lys-NH2] | 1 | 96 | 97 | 100 | 100 |
| Cyclo2,7 [Ac-Nle-Asp- | His- | D-MePhe- | MeArg- | Trp-Lys-NH2] | 1 | 39 | | 39 | |
| Cyclo2,7 [Ac-Nle-Asp- | His- | D-Phe(3-Cl)— | Arg- | Trp-Lys-NH2] | 1 | 84 | 77 | 99 | 85 |
| Cyclo1,6 [heptanoyl-Asp- | His- | D-Phe- | Arg- | Trp-Lys-OH] | 1 | 73 | | 97 | |
| Cyclo2,7 [Ac-Nle-Asp- | His- | D-Phe(2-Cl)— | Arg- | Trp-Lys-NH2] | 0.1 | 99 | | 100 | |
| Cyclo2,7 [Ac-Nle-Asp- | His- | D-Tiq- | Arg- | Trp-Lys-NH2] | 1 | 20 | | 15 | |
| Cyclo1,6 [heptanoyl-Asp- | Ser(Bzl)- | D-Phe(3-Cl)— | Arg- | Trp-Lys-NH2] | 1 | 66 | 92 | 100 | 97 |
| Cyclo1,6 [heptanoyl-Asp- | Ser(Bzl)- | D-Phe(3-Cl)— | Arg- | Trp-Lys-NH2] | 0.1 | 64 | | 99 | |
| Cyclo1,6 [heptanoyl-Asp- | Ser(Bzl)- | D-Phe(3-Cl)— | Arg- | Trp-Lys-NH2] | 0.01 | 28 | | 88 | |
| Cyclo1,6 [heptanoyl-Asp- | Ser(Bzl)- | D-Phe(3-Cl)— | Arg- | Trp-Lys-NH2] | 0.001 | 13 | | 25 | |
| Cyclo1,6 [heptanoyl-Asp- | His- | D-Phe(3-Cl)— | Arg- | Nal 2'-Lys-NH2] | 0.01 | 73 | | 82 | |
| Cyclo1,6 [heptanoyl-Asp- | His- | D-Phe(3-Cl)— | Arg- | Nal 2'-Lys-NH2] | 0.001 | 42 | | 7 | |
| Cyclo1,6 [heptanoyl-Asp- | His- | D-Phe(3-Cl)— | Arg- | Nal 2'-Lys-NH2] | 0.0001 | 18 | | 0 | |
| Cyclo1,6 [heptanoyl-Asp- | Thr(Bzl)- | D-Phe(3-Cl)— | Arg- | Trp-Lys-NH2] | 1 | 59 | 79 | 99 | 91 |
| Cyclo1,6 [heptanoyl-Asp- | Ser(Bzl)- | D-Phe(3-Cl)— | Arg- | D-Trp-Lys-NH2] | 1 | 66 | 90 | 98 | 99 |
| Cyclo1,6 [2-Naphthylacetyl-Asp- | Ser(Bzl)- | D-Phe(3-Cl)— | Arg- | Trp-Lys-NH2] | 1 | 5 | 68 | 88 | 69 |
| Cyclo1,6 [heptanoyl-Asp- | His- | D-Phe(3-Cl)— | Arg- | Trp-Lys-NH2] | 1 | 94 | 78 | 97 | 71 |
| cyclo1,5[2-Naphthylacetyl-Asp | — | D-Phe(2-Cl)— | Arg- | Trp-Lys-NH2] | 1 | 19 | 7 | 67 | 20 |
| cyclo1,6[2-Naphthylacetyl-Asp- | Ala- | D-Phe(2-Cl)— | Arg- | Trp-Lys-NH2] | 1 | 62 | 82 | 98 | 73 |
| cyclo2,7[Ac-Nle-Asp- | His- | D-Me(homo) Phe- | Arg- | Trp-Lys-NH2] | 1 | 2 | 4 | 0 | 2 |
| cyclo2,7[Ac-Nle-Asp- | His- | D-EtPhe- | Arg- | Trp-Lys-NH2] | 1 | 80 | 37 | 53 | 39 |
| cyclo2,7[Ac-Nle-Asp- | His- | D-Phe- | MeArg- | MeTrp-Lys-NH2] | 1 | 94 | 3 | 53 | 29 |
| cyclo2,7[Ac-Nle-Asp- | MeHis- | D-Phe- | Arg- | Trp-Lys-NH2] | 1 | N.D. | N.D. | N.D. | N.D. |

The invention is further illustrated by the following non-limiting examples.

EXAMPLE 1

The Ki (nM) of certain peptides were determined, as was the agonist/antagonist status with respect to MC4-R. Functional evaluation of peptides at MC4-R was performed by measuring the accumulation of intracellular cAMP in HEK-293 cells expressing MC4-R. Antagonistic activity was determined by measuring the inhibition of α-MSH-induced cAMP levels following exposure to the compounds. Cells, suspended in Earle's Balanced Salt Solution containing 10 mM HEPES, pH 7.5, 5 mM MgCl2, 1 mM glutamine, 0.1% albumin and 0.6 mM 3-isobutyl-1-methyl-xanthine, a phosphodiesterase inhibitor, were plated in 96 well plates at a density of $0.5 \times 10^5$ cells per well. Cells were incubated with the test peptides in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software.

TABLE 5

| | Ki (nM) | | | HEK-293 | |
|---|---|---|---|---|---|
| | MC-1 B-16 | MC-3 Mem | MC-4 Mem | MC-5 Mem | (MC4-R) cells Classification |
| 7'-amino-heptanoyl-Ser(Bzl)-D-Nal 2-Arg-Trp-NH2 | 1865 | 50 | 4 | 102 | Antagonist |
| 7'-amino-heptanoyl-Ser(Bzl)-D-Nal 2-Arg-D-Trp-NH2 | 1296 | 70 | 6 | 90 | Antagonist |
| 7'-amino-heptanoyl-Ser(Bzl)-D-Phe(4-Cl)-Arg-Trp-Asp-NH2 | 760 | 191 | 9 | 596 | Agonist |
| 7'-amino-heptanoyl-Ser(Bzl)-D-Phe(4-Cl)-Arg-Trp-Asp-Phe-NH2 | 269 | 318 | 12 | 386 | Agonist |
| 7'-amino-heptanoyl-Ser(Bzl)-D-Phe(4-Cl)-Arg-Trp-Ala-NH2 | 142 | 37 | 2 | 112 | Agonist |

TABLE 5-continued

| | Ki (nM) | | | HEK-293 |
|---|---|---|---|---|
| | MC-1 B-16 | MC-3 Mem | MC-4 Mem | MC-5 (MC4-R) cells Mem Classification |
| 7'-amino-heptanoyl-Ser(Bzl)-D-Phe(4-Cl)-Arg-Trp-NH$_2$ | 795 | 25 | 1 | 175 Agonist |

FIG. 1 is a graph of displacement of I$^{125}$-NDP-α-MSH bound to MC1-R, MC3-R, MC4-R and MC5-R using varying concentrations of 7'-amino-heptanoyl-Ser(Bzl)-D-Phe(4'-Cl)-Arg-Trp-NH$_2$, showing the binding affinity curves.

EXAMPLE 2

Figure 2:
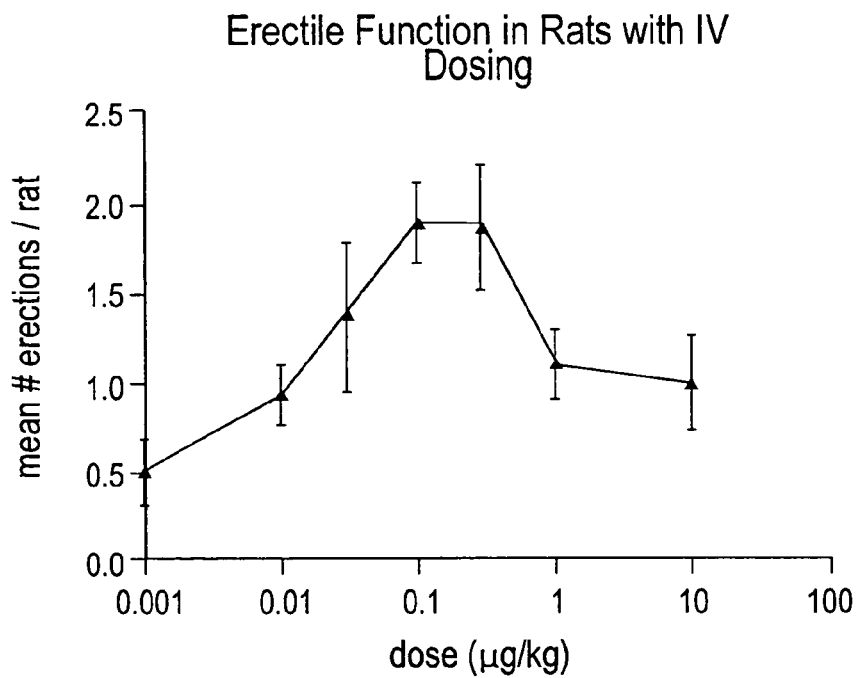
FIG. 2 is a graph showing erectile activity in rats with iv administration of varying quantities of 7'-amino-heptanoyl-Ser(Bzl)-D-Phe(4-Cl)-Arg-Trp-NH$_2$.

The ability of compounds to induce penile erection (PE) in male rats was evaluated with selected peptides. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with peptides at a variety of doses via intravenous (IV), subcutaneous (SC), intracerebroventricular (ICV), intraperitoneal (IP) injection or administered intranasally (IN) using a micropipetor to deliver 25 µL of solution into one nostril. Immediately after treatment, rats were placed into individual polystyrene cages (27 cm long, 16 cm wide, and 25 cm high) for behavioral observation. Rats were observed for 30 minutes and the number of yawns, grooming bouts and PEs were recorded in three 10-minute bins. As shown in FIG. 2, selected peptides, including 7'-amino-heptanoyl-Ser(Bzl)-D-Phe(4'-Cl)-Arg-Trp-NH$_2$, induced erections in male rats.

EXAMPLE 3

Figure 3:
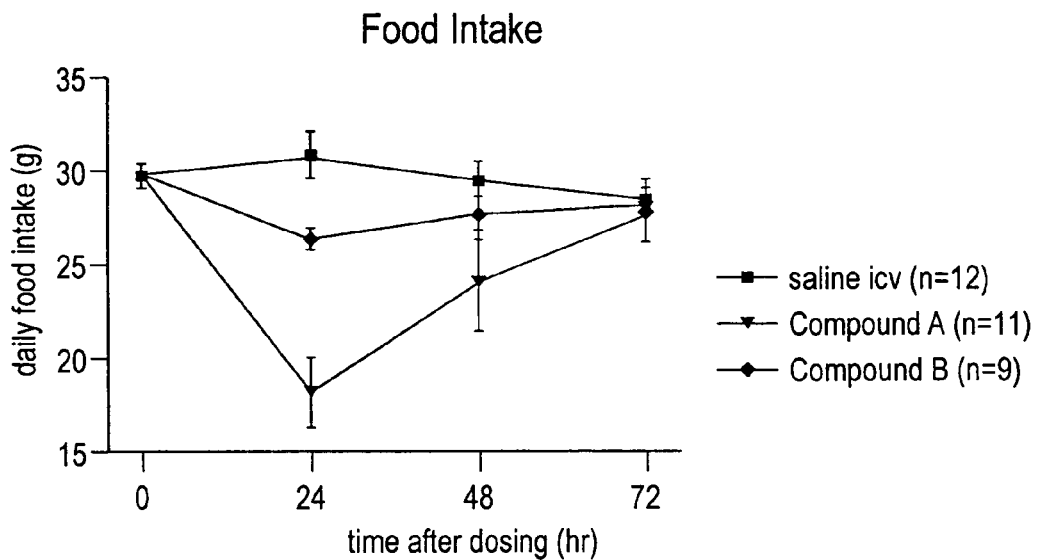
FIG. 3 is a graph of food intake in male Sprague-Dawley rats administered saline or test compounds by intracerebroventricular (ICV) dosing. Saline was given to 12 animals, Compound A (7'-amino-heptanoyl-Ser(Bzl)-D-Phe(4-Cl)-Arg-Trp-Asp-Phe-NH$_2$) was given to 11 animals and Compound B (heptanoyl-Thr(Bzl)-D-Phe(4-Cl)-Arg-Trp-NH$_2$) was administered to 9 animals. At 24 hours the difference in food intake for Compound A compared to saline treatment was significant at a p value of <0.01.
Figure 4:
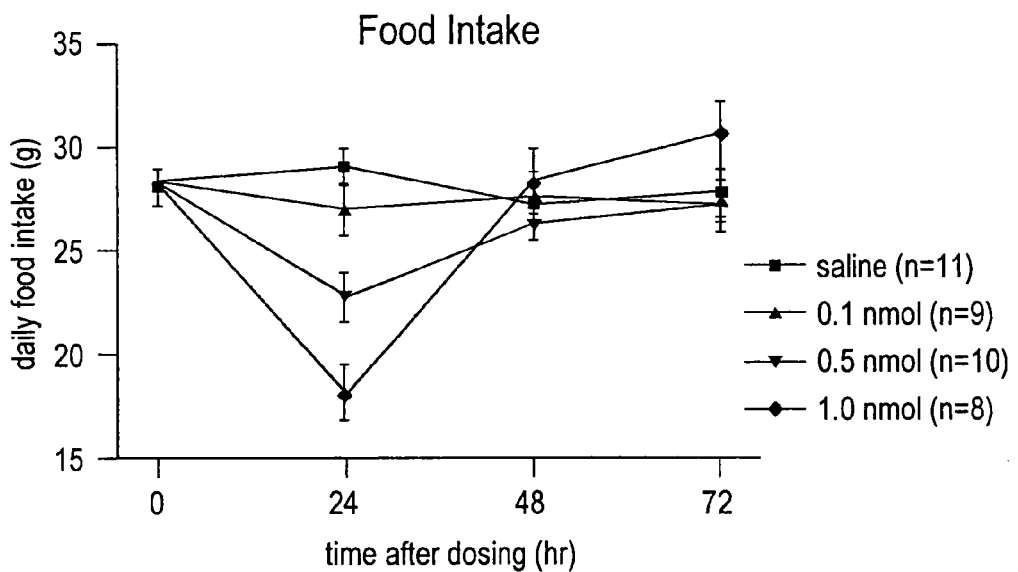
FIG. 4 is a graph of food intake in male Sprague-Dawley rats administered saline or different doses of 7'-amino-heptanoyl-Ser(Bzl)-D-Phe(4-Cl)-Arg-Trp-NH$_2$ by ICV, with the number of animals in each group shown. The difference in food intake at 24 hours for 1.0 nmol was significant at a p<0.01, and for 0.5 nmol was significant at a p<0.05 when compared to saline treatment. Animals receiving saline had an average daily body weight gain of 4 g, animals receiving 0.1 nmol gained 3 g, animals receiving 0.5 nmol lost 1 g and animals receiving 1.0 nmol lost 3 g. These animals returned to baseline by 48 hours after dosing.
Figure 5:
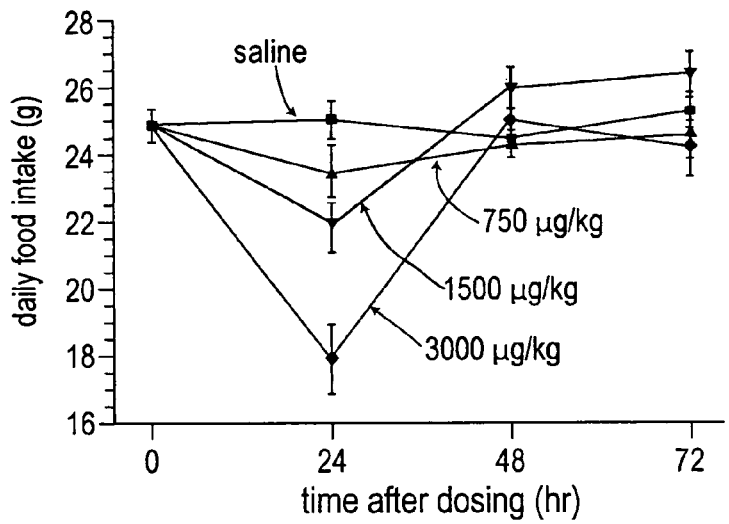
FIG. 5 is a graph of food intake in male Sprague-Dawley rats administered saline or different doses of 7'-amino-heptanoyl-Ser(Bzl)-D-Phe(4-Cl)-Arg-Trp-NH$_2$ by intraperitoneal (IP) dosing. 12 animals were in each of the four groups (saline, 750 μg/kg, 1500 μg/kg and 3000 μg/kg). The difference in food intake for both 1500 μg/kg and 3000 μg/kg at 24 hours was significant at a p value of <0.01. Animals receiving saline had an average daily body weight gain of 4 g, animals receiving 750 μg/kg gained 4 g, animals receiving 1500 μg/kg gained 2 g and animals receiving 3000 μg/kg lost 1 g.

Food intake and body weight change was evaluated for selected peptides. Male Sprague-Dawley rats weighing ~300 g at the beginning of the experiment were kept on a 12 hour on/of light cycle. Lights out was adjusted to 12:00 p.m. to allow for dosing just prior to the start of their dark period. Rats (12/group) were fed powdered chow and water ad libitum. For 1 week before treatment, 24-hour food intake and body weight change was recorded to assess a baseline for the group during vehicle treatment. The rats were dosed ICV, IV, SC or IP on day 0 and food intake and body weight measured daily for 1 week. Animals were dosed once per week for up to 6 weeks and their food intake and daily weight changed compared to their baseline. FIGS. 3, 4 and 5 illustrate results of different peptides at different doses and by varying routes of administration.

EXAMPLE 4

Figure 6:
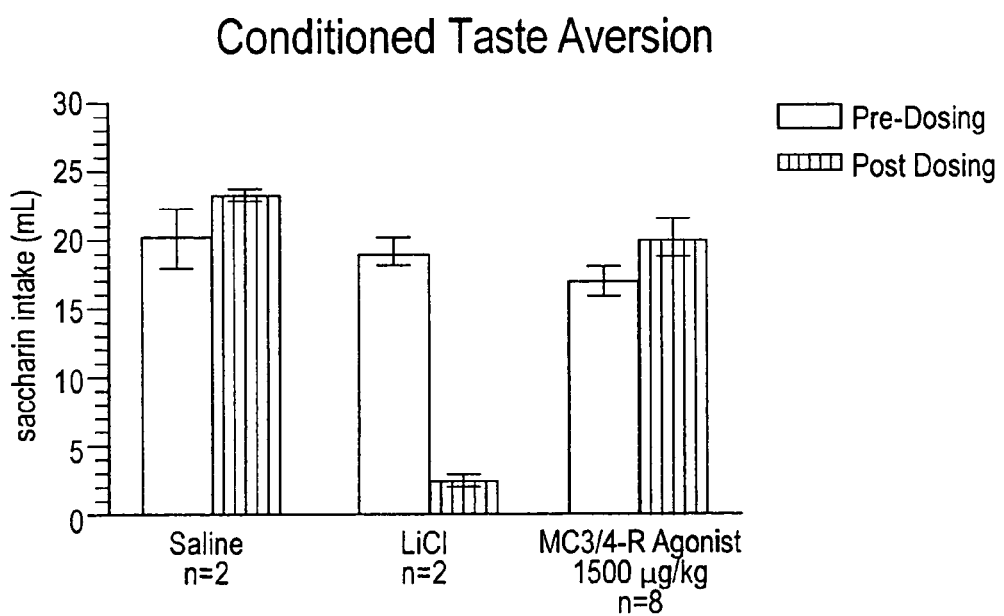
FIG. 6 is a graph illustrating no conditioned taste aversion response to 7'-amino-heptanoyl-Ser(Bzl)-D-Phe(4-Cl)-Arg-Trp-NH$_2$, thereby demonstrating that observed weight lost is not due to induced illness or similar side effects. Both predosing and post-dosing consumption of water with saccharin added was measured, with dosing consisting of IP administration of saline (negative control), LiCl (positive control) and the test article, 7'-amino-heptanoyl-Ser(Bzl)-D-Phe(4-Cl)-Arg-Trp-NH$_2$, administered at 1500 μg/kg.

Conditioned taste aversion was evaluated in rats using selected peptides. Male Sprague-Dawley rats weighing ~300 g were kept on a 12 hour on/of light cycle. Lights out was adjusted to 12:00 p.m. with food ad libitum. Animals were trained to be accustomed to 30 minutes of access to water per day. On day 1 of the experiment, rats were given 30 minutes of access to water containing 0.15% saccharin immediately prior to being dosed ICV, IV or IP with compound. On day 2 they were given plain water for the appointed time. On day 3 the rats were given saccharin-containing water again. The amount of fluid these animals consumed on day 1 and day 3 was compared. Reduced intake on day 3 indicates a conditioned taste aversion due to illness induced by drug treatment on day 1. LiCl treatment (127 mg/kg; IP) was used as a positive control. The results of FIG. 6 illustrates that 7'-amino-heptanoyl-Ser(Bzl)-D-Phe(4'-Cl)-Arg-Trp-NH$_2$, administered IP at 1500 µg/kg, did not induce a conditioned taste aversion response, illustrating that the decreased food intake in FIGS. 4 and 5 was not due to aversive effect of 7'-amino-heptanoyl-Ser(Bzl)-D-Phe(4'-Cl)-Arg-Trp-NH$_2$.

Each of the foregoing is merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above are hereby incorporated by reference.

The preceding examples can be repeated with similar success by substituting the generically or specifically described reactants and/or operating conditions of this invention for those used in the preceding examples.

What is claimed is:

1. A peptide, consisting of the sequence $S_1$-$S_2$-D-Phe(4-Cl)-$S_4$-$S_5$, wherein $S_1$ is heptanoyl, 2'-naphthylacetyl, 7'-amino-heptanoyl, 2'-chlorophenylacetyl, 3'-chlorophenylacetyl, 4'-chlorophenylacetyl, 4'-phenylbutylaminocarbonyl, 3'-phenylbutylaminocarbonyl, 4'-bromophenyl-acetyl, 3-4-dichlorophenyl-acetyl, 2,4-dichlorophenyl-acetyl, 4-biphenyl-acetyl, 2-naphthoyl, Ph-$(CH_2)_2$NH, 3'-phenylpropanecarbonyl, 2'-naphthoyl-Pip, 2'-naphthylacetyl, 2'-bromophenyl-acetyl, 4'-CF$_3$phenyl-acetyl, 3'-CF$_3$phenyl-acetyl, 2'-CF$_3$phenyl-acetyl, 3',5'-CF$_3$phenylacetyl, 2',5'-CF$_3$phenylacetyl, 4'-Mephenyl-acetyl, 3'-Mephenyl-acetyl, 2'-Mephenyl-acetyl, 7'-aminoheptonoyl, beta-Ala, 4-aminoBytyl, 5-aminoValeryl, 6-aminoCaproyl, aminoTranexamyl, Cmpi or 3',4'-Cl$_2$phenylacetyl;

S$_2$ is absent or is Ser(Bzl), Ala, D-Ala, beta-Ala, Val, Leu, Chg, Aib, Tle, 1-amino-1cyclohexanecarbonyl, Inp, CO(CH$_2$)$_2$NH, CO(CH$_2$)$_2$CO, Pip, MeThr(Bzl), Thr (Bzl) or D-Thr(Bzl);

S$_4$ is Arg, D-Arg, (Nlys)Gly, Trp, Lys, homoLys, Dpr(beta-Ala), alpha-(N-amidino-4'-piperidine)Gly, (4'-guanidino)Gly, (4'-guanidino)Phe, D-(4'-guanidino)Phe, beta-(N-amidino-4'-peperidine)Ala or homo-Ala-4'-pip (N-amidino); and S$_5$ is Trp, Trp-OH, Trp-NH$_2$, D-Trp, D-Trp-NH$_2$, Trp-Val-NH$_2$, 3'-Pya-NH$_2$, Phe-NH$_2$, MeTrp-NH$_2$, beta-Ala-Trp-NH$_2$, aminobutylamide, Nal 1-NH$_2$, D-Nal 1-NH$_2$, Nal 2-NH$_2$, D-Nal 2-NH$_2$, Tic-NH$_2$, D-Tic-NH$_2$, 1'-aminoindan, 1'-aminoindane-1-carboxyl-NH$_2$, Aic-NH$_2$, Atc-NH$_2$, Disc-NH$_2$, Tpi-NH$_2$, D-Tpi-NH$_2$, Tiq-NH$_2$, D-Tiq-NH$_2$, tryptamide, NMe-tryptamide, alpha-Me-tryptamide, 2'-(4'-methylphenyl)ethylamide, 3',4'-Cl$_2$)phenylmethylamide, 3'-phenylpropylamide, 2',4'-dichlorobenzylamide, 3'-(1H-imidazol)propylamide, 4-phenyl-piperidine-4-carbonamide, 3-phenyl-1-propylamide, 2,4-dichlorophenethylamide, S-(−)-1-(2-naphthyl)ethylamide, S-(−)-1-(1-naphthyl)ethylamide, 2'-methylbenzylamide, 4'-methylbenzylamide, 2',2'-diphenylethylamide, 1-(2-pyridyl)piperazine, N-benzylmethylamide, histamide, R-(+)-1-(2-Naphthyl)ethylamide, Trp-Asp-NH$_2$, Trp-Asp-Phe-NH$_2$, Asp-Trp-NH$_2$, Ala-Trp-NH$_2$, Trp-Ala-NH$_2$, phenethylamide or Trp-Asp-OH.

2. The peptide of claim 1 consisting of the sequence:
7'-amino-heptanoyl-Ser(Bzl)-D-Phe(4-Cl)-Arg-Trp-NH$_2$,
7'-amino-heptanoyl-Ser(Bzl)-D-Phe(4-Cl)-Arg-Trp-Ala-NH$_2$,
7'-amino-heptanoyl-Ser(Bzl)-D-Phe(4-Cl)-Arg-Trp-Asp-Phe-NH$_2$,
7'-amino-heptanoyl-Ser(Bzl)-D-Phe(4-Cl)-Arg-Trp-Asp-NH$_2$,
heptanoyl-Thr(Bzl)-D-Phe(4-Cl)-Arg-Trp-NH$_2$,
7'-amino-heptanoyl-Ser(Bzl)-D-Phe(4-Cl)-Arg-MeTrp-NH$_2$,
heptanoyl-Ser(Bzl)-D-Phe(4-Cl)-Arg-MeTrp-NH$_2$,
7'-amino-heptanoyl-Ser(Bzl)-D-Phe(4-Cl)-Arg-Tryptamide,
7'-amino-heptanoyl-Ser(Bzl)-D-Phe(4-Cl)-Arg-NMe-Tryptamide,
7'-amino-heptanoyl-Ser(Bzl)-D-Phe(4-Cl)-Arg-alpha-Me-Tryptamide,
7'-amino-heptanoyl-Ser(Bzl)-D-Phe(4-Cl)-Arg-S-(−)-1-(1-Naphthyl)ethylamide,
7'-amino-heptanoyl-Ser(Bzl)-D-Phe(4-Cl)-Arg-Nal 1-NH$_2$,
7'-amino-heptanoyl-Ser(Bzl)-D-Phe(4-Cl)-Arg-D-Nal 2-N H$_2$,
7'-amino-heptanoyl-Ser(Bzl)-D-Phe(4-Cl)-Arg-Nal 2-NH$_2$,
2'-naphthylacetyl-Ala-D-Phe(4-Cl)-Arg-Trp-NH$_2$,
4'phenylbutyryl-Ala-D-Phe(4-Cl)-Arg-Trp-NH$_2$,
3',4'-dichlorophenyl-acetyl-Ala-D-Phe(4-Cl)-Arg-Trp-NH$_2$, or
3'-CF$_3$phenyl-acetyl-Ala-D-Phe(4-Cl)-Arg-Trp-NH$_2$.

3. A peptide, consisting of the sequence 7'-amino-heptanoyl-S$_2$-D-Phe(4-Cl)-S$_4$-S$_5$, wherein S$_2$ is absent or is Ser(Bzl), Ala, D-Ala, beta-Ala, Val, Leu, Chg, Aib, Tle, 1-amino-1cyclohexanecarbonyl, Inp, CO(CH$_2$)$_2$NH, CO(CH$_2$)$_2$CO, Pip, MeThr(Bzl), Thr (Bzl) or D-Thr(Bzl);

S$_4$ is Arg, D-Arg, (Nlys)Gly, Trp, Lys, homoLys, Dpr(beta-Ala), alpha-(N-amidino-4'-piperidine)Gly, (4'-guanidino)Gly, (4'-guanidino)Phe, D-(4'-guanidino)Phe, beta-(N-amidino-4'-peperidine)Ala or homo-Ala-4'-pip (N-amidino); and S$_5$ is Trp, Trp-OH, Trp-NH$_2$, Trp-Cys-NH$_2$, D-Trp, D-Trp-NH$_2$, Trp-Val-NH$_2$, 3'-Pya-NH$_2$, Phe-NH$_2$, MeTrp-NH$_2$, beta-Ala-Trp-NH$_2$, aminobutylamide, Nal 1-NH$_2$, D-Nal 1-NH$_2$, Nal 2-NH$_2$, D-Nal 2-NH$_2$, Tic-NH$_2$, D-Tic-NH$_2$, 1'-aminoindan, 1'-aminoindane-1-carboxyl-NH$_2$, Aic-NH$_2$, Atc-NH$_2$, Disc-NH$_2$, Tpi-NH$_2$, D-Tpi-NH$_2$, Tiq-NH$_2$, D-Tiq-NH$_2$, tryptamide, NMe-tryptamide, alpha-Me-tryptamide, 2'-(4'-methylphenyl)ethylamide, 3',4'-Cl$_2$)phenylmethylamide, 3'-phenylpropylamide, 2',4'-dichlorobenzylamide, 3'-(1H-imidazol)propylamide, 4-phenyl-piperidine-4-carbonamide, 3-phenyl-1-propylamide, 2,4-dichlorophenethylamide, S-(−)-1-(2-naphthyl)ethylamide, S-(−)-1-(1-naphthyl)ethylamide, 2'-methylbenzylamide, 4'-methylbenzylamide, 2',2'-diphenylethylamide, 1-(2-pyridyl)piperazine, N-benzylmethylamide, histamide, R-(+)-1-(2-Naphthyl)ethylamide, Trp-Asp-NH$_2$, Trp-Asp-Phe-NH$_2$, Asp-Trp-NH$_2$, Ala-Trp-NH$_2$, Trp-Ala-NH$_2$, phenethylamide or Trp-Asp-OH.

4. The peptide of claim 3 consisting of the sequence
7'-amino-heptanoyl-Ser(Bzl)-D-Phe(4-Cl)-Arg-Trp-Ala-NH$_2$,
7'-amino-heptanoyl-Ser(Bzl)-D-Phe(4-Cl)-Arg-Trp-Asp-Phe-NH$_2$,
7'-amino-heptanoyl-Ser(Bzl)-D-Phe(4-Cl)-Arg-Trp-Asp-NH$_2$,
7'-amino-heptanoyl-Ser(Bzl)-D-Phe(4-Cl)-Arg-MeTrp-NH$_2$,
7'-amino-heptanoyl-Ser(Bzl)-D-Phe(4-Cl)-Arg-Tryptamide,
7'-amino-heptanoyl-Ser(Bzl)-D-Phe(4-Cl)-Arg-NMe-Tryptamide,
7'-amino-heptanoyl-Ser(Bzl)-D-Phe(4-Cl)-Arg-alpha-Me-Tryptamide,
7'-amino-heptanoyl-Ser(Bzl)-D-Phe(4-Cl)-Arg-S-(−)-1-(1-Naphthyl)ethylamide,
7'-amino-heptanoyl-Ser(Bzl)-D-Phe(4-Cl)-Arg-Nal 1-NH$_2$,
7'-amino-heptanoyl-Ser(Bzl)-D-Phe(4-Cl)-Arg-D-Nal 2-NH$_2$, or
7'-amino-heptanoyl-Ser(Bzl)-D-Phe(4-Cl)-Arg-Nal 2-NH$_2$.

5. A peptide, consisting of the sequence S$_1$-S$_2$-S$_3$-S$_4$-S$_5$, wherein

S$_1$ is heptanoyl, 2'-naphthylacetyl, 7'-amino-heptanoyl, 2'-chlorophenylacetyl, 3'-chlorophenylacetyl, 4'-chlorophenylacetyl, 4'-phenylbutylaminocarbonyl, 3'-phenylbutylaminocarbonyl, 4'-bromophenyl-acetyl, 3-4-dichlorophenyl-acetyl, 2,4-dichlorophenyl-acetyl, 4-biphenyl-acetyl, 2-naphthoyl, Ph-(CH$_2$)$_2$NH, 3'-phenylpropanecarbonyl, 2'-naphthoyl-Pip, 2'-naphthylacetyl, 2'-bromophenyl-acetyl, 4'-CF$_3$phenyl-acetyl, 3'-CF$_3$phenyl-acetyl, 2'-CF$_3$phenyl-acetyl, 3',5'-CF$_3$phenylacetyl, 2',5'-CF$_3$phenylacetyl, 4'-Mephenyl-acetyl, 3'-Mephenyl-acetyl, 2'-Mephenyl-acetyl, 7'-aminoheptonoyl, beta-Ala, 4-aminoBytyl, 5-aminoV-aleryl, 6-aminoCaproyl, aminoTranexamyl, Cmpi or 3',4'-Cl$_2$phenylacetyl;

S$_2$ is absent or is Ser(Bzl), Ala, D-Ala, beta-Ala, Val, Leu, Chg, Aib, Tle, 1-amino-1cyclohexanecarbonyl, Inp, CO(CH$_2$)$_2$NH, CO(CH$_2$)$_2$CO, Pip, MeThr(Bzl), Thr (Bzl) or D-Thr(Bzl);

S$_3$ is Phe, D-Phe, Phe(4-Cl), D-Phe(4-Cl), Phe(3-Cl), D-Phe(3-Cl), Phe(2-Cl), D-Phe(2-Cl), D-Phe(3,4-diCl), MePhe, D-MePhe, D-Tic, D-Tpi, D-Nal 2, Arg, D-Phe (3,4-F$_2$), D-Tiq, D-Me(homo)Phe or D-EtPhe;

S$_4$ is Arg, D-Arg, (Nlys)Gly, Trp, Lys, homoLys, Dpr(beta-Ala), alpha-(N-amidino-4'-piperidine)Gly, (4'-guanidino)Gly, (4'-guanidino)Phe, D-(4'-guanidino)Phe, beta-(N-amidino-4'-peperidine)Ala or homo-Ala-4'-pip (N-amidino); and S$_5$ is Trp, Trp-OH, Trp-NH$_2$, D-Trp, D-Trp-NH$_2$, Trp-Val-NH$_2$, 3'-Pya-NH$_2$, Phe-NH$_2$, MeTrp-NH$_2$, beta-Ala-Trp-NH$_2$, aminobutylamide, Nal 1-NH$_2$, D-Nal 1-NH$_2$, Nal 2-NH$_2$, D-Nal 2-NH$_2$, Tic-NH$_2$, D-Tic-NH$_2$, 1'-aminoindan, 1'-aminoindane-1-carboxyl-NH$_2$, Aic-NH$_2$, Atc-NH$_2$, Disc-NH$_2$, Tpi-NH$_2$, D-Tpi-NH$_2$, Tiq-NH$_2$, D-Tiq-NH$_2$, tryptamide, NMe-tryptamide, alpha-Me-tryptamide, 2'-(4'-methylphenyl)ethylamide, 3',4'-Cl$_2$) phenylmethylamide, 3'-phenylpropylamide, 2',4'-dichlorobenzylamide, 3'-(1H-imidazol)propylamide, 4-phenyl-piperidine-4-carbonamide, 3-phenyl-1-propylamide, 2,4-dichlorophenethylamide, S-(−)-1-(2-naphthyl)ethylamide, S-(−)-1-(1-naphthyl)ethylamide, 2'-methyl benzylamide, 4'-methylbenzylamide, 2',2'-diphenylethylamide, 1-(2-pyridyl)piperazine, N-benzylmethylamide, histamide, R-(+)-1-(2-Naphthyl)ethylamide, Trp-Asp-NH$_2$, Trp-Asp-Phe-NH$_2$, Asp-Trp-NH$_2$, Ala-Trp-NH$_2$, Trp-Ala-NH$_2$, phenethylamide or Trp-Asp-OH.

6. The peptide of claim 5 consisting of the sequence
7'-amino-heptanoyl-Ser(Bzl)-D-Phe(4-Cl)-Arg-Trp,
7'-amino-heptanoyl-Ser(Bzl)-D-Phe(4-Cl)-Arg-Trp-NH$_2$,
7'-amino-heptanoyl-Ser(Bzl)-D-Phe(4-Cl)-Arg-Trp-Ala-NH$_2$,
7'-amino-heptanoyl-Ser(Bzl)-D-Phe(4-Cl)-Arg-Trp-Asp-Phe-NH$_2$,
7'-amino-heptanoyl-Ser(Bzl)-D-Phe(4-Cl)-Arg-Trp-Asp-NH$_2$,
heptanoyl-Thr(Bzl)-D-Phe(4-Cl)-Arg-Trp-NH$_2$,
7'-amino-heptanoyl-Ser(Bzl)-D-Nal 2-Arg-Trp-NH$_2$,
7'-amino-heptanoyl-Ala-D-Nal 2-Arg-Trp-NH$_2$,
Ser(Bzl)-D-Nal 2-Arg-Trp-NH$_2$,
Ser(Bzl)-D-Nal 2-Arg-D-Trp-NH$_2$,
7'-amino-heptanoyl-Ser(Bzl)-D-Phe(4-Cl)-Arg-MeTrp-NH$_2$,
heptanoyl-Ser(Bzl)-D-Phe(4-Cl)-Arg-MeTrp-NH$_2$,
7'-amino-heptanoyl-Ser(Bzl)-D-Phe(4-Cl)-Arg-Tryptamide,
7'-amino-heptanoyl-Ser(Bzl)-D-Phe(4-Cl)-Arg-NMe-Tryptamide,
7'-amino-heptanoyl-Ser(Bzl)-D-Phe(4-Cl)-Arg-alpha-Me-Tryptamide,
7'-amino-heptanoyl-Ser(Bzl)-D-Phe(4-Cl)-Arg-S-(−)-1-(1-Naphthyl)ethylamide,
7'-amino-heptanoyl-Ser(Bzl)-D-Phe(4-Cl)-Arg-Nal 1-NH$_2$,
7'-amino-heptanoyl-Ser(Bzl)-D-Phe(4-Cl)-Arg-D-Nal 2-N H$_2$,
7'-amino-heptanoyl-Ser(Bzl)-D-Phe(4-Cl)-Arg-Nal 2-NH$_2$,
2'-naphthylacetyl-Ala-D-Phe(4-Cl)-Arg-Trp-NH$_2$,
4' phenylbutyryl-Ala-D-Phe(4-Cl)-Arg-Trp-NH$_2$,
3',4'-dichlorophenyl-acetyl-Ala-D-Phe(4-Cl)-Arg-Trp-NH$_2$, or
3'-CF$_3$phenyl-acetyl-Ala-D-Phe(4-Cl)-Arg-Trp-NH$_2$.

7. A peptide of the sequence 7'-amino-heptanoyl-Ser(Bzl)-D-Phe(4-Cl)-Arg-Trp-NH$_2$.

8. A pharmaceutical composition comprising a peptide of the sequence 7'-amino-heptanoyl-Ser (Bzl)-D-Phe(4-Cl)-Arg-Trp-NH$_2$.

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: partial sequence of alpha-melanocyte
      stimulating hormone

<400> SEQUENCE: 1

His Phe Arg Trp
1

<210> SEQ ID NO 2
<211> LENGTH: 5
<212> TYPE: PRT

```
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: 7'-amino-heptanoyl
<220> FEATURE:
<221> NAME/KEY: MISC_FEATURE
<222> LOCATION: (2)..(2)
<223> OTHER INFORMATION: Ser(Bzl)
<220> FEATURE:
<221> NAME/KEY: MISC_FEATURE
<222> LOCATION: (3)..(3)
<223> OTHER INFORMATION: Phe(4-Cl)
<220> FEATURE:
<221> NAME/KEY: MOD_RES
<222> LOCATION: (5)..(5)
<223> OTHER INFORMATION: AMIDATION

<400> SEQUENCE: 2

Xaa Xaa Xaa Arg Trp
1               5

<210> SEQ ID NO 3
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Nle
<220> FEATURE:
<221> NAME/KEY: MOD_RES
<222> LOCATION: (7)..(7)
<223> OTHER INFORMATION: AMIDATION

<400> SEQUENCE: 3

Xaa Asp His His Arg Trp Lys
1               5

<210> SEQ ID NO 4
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 4

His Phe Cys Trp
1
```